US012679818B2

(12) United States Patent
Tanaka et al.

(10) Patent No.: US 12,679,818 B2
(45) Date of Patent: Jul. 14, 2026

(54) RADIOACTIVE HALOGEN LABELING PRECURSOR COMPOUND

(71) Applicants: INSTITUTE OF SCIENCE TOKYO, Tokyo (JP); FUKUSHIMA MEDICAL UNIVERSITY, Fukushima (JP); TAIYO NIPPON SANSO CORPORATION, Tokyo (JP)

(72) Inventors: Hiroshi Tanaka, Tokyo (JP); Kazuhiro Takahashi, Fukushima (JP); Miho Suzuki, Fukushima (JP)

(73) Assignees: Institute of Science Tokyo, Tokyo (JP); Fukushima Medical University, Fukushima (JP); Taiyo Nippon Sanso Corporation, Tokyo (JP)

( * ) Notice: Subject to any disclaimer, the term of this patent is extended or adjusted under 35 U.S.C. 154(b) by 405 days.

(21) Appl. No.: 18/037,038

(22) PCT Filed: Jan. 18, 2022

(86) PCT No.: PCT/JP2022/001558

§ 371 (c)(1),
(2) Date: May 15, 2023

(87) PCT Pub. No.: WO2022/158442

PCT Pub. Date: Jul. 28, 2022

(65) Prior Publication Data

US 2024/0034721 A1 Feb. 1, 2024

(30) Foreign Application Priority Data

Jan. 19, 2021 (JP) ................................ 2021-006394

(51) Int. Cl.

| | |
|---|---|
| ***C07D 319/06*** | (2006.01) |
| ***C07B 59/00*** | (2006.01) |
| ***C07C 309/83*** | (2006.01) |
| ***C07D 405/06*** | (2006.01) |
| ***C07D 407/12*** | (2006.01) |

(52) U.S. Cl.

CPC .......... *C07D 319/06* (2013.01); *C07B 59/002* (2013.01); *C07C 309/83* (2013.01); *C07D 405/06* (2013.01); *C07D 407/12* (2013.01)

(58) Field of Classification Search

None

See application file for complete search history.

(56) References Cited

U.S. PATENT DOCUMENTS

| | | | |
|---|---|---|---|
| 2,852,554 | A | 9/1958 | England et al. |
| 2007/0274911 | A1 | 11/2007 | Brown et al. |
| 2012/0329968 | A1 | 12/2012 | Takahashi et al. |
| 2020/0009273 | A1 | 1/2020 | Kiriu et al. |

FOREIGN PATENT DOCUMENTS

| | | | |
|---|---|---|---|
| EP | 2 657 213 | A1 | 10/2013 |
| JP | 2007-500688 | A | 1/2007 |
| WO | WO 2011/099480 | A1 | 8/2011 |
| WO | WO 2018/164043 | A1 | 9/2018 |
| WO | WO 2019/151384 | A1 | 8/2019 |

OTHER PUBLICATIONS

Sasaki. Organic and Biomolecular Chemistry, 2023, 21, 7467-7472. (Year: 2023).*

Yang. Chemical Reviews, 2017, 117, pp. 12281-12356 (Year: 2017).*

Extended European Search Report for European Application No. 22742564.2, dated Nov. 21, 2024.

Stang et al., "Perfluoroalkanesulfonic Esters: Methods of Preparation and Applications in Organic Chemistry," Synthesis, XP002521747, Feb. 1982, pp. 85-126 and p. 1164.

International Preliminary Report on Patentability, dated Aug. 3, 2023, and English translation of the Written Opinion of the International Searching Authority, dated Mar. 15, 2022, for International Application No. PCT/JP2022/001558.

International Search Report for PCT/JP2022/001558 (PCT/ISA/210) mailed on Mar. 15, 2022.

Written Opinion of the International Searching Authority for PCT/JP2022/001558 (PCT/ISA/237) mailed on Mar. 15, 2022.

* cited by examiner

*Primary Examiner* — Noble E Jarrell

(74) *Attorney, Agent, or Firm* — Birch, Stewart, Kolasch & Birch, LLP

(57) ABSTRACT

Provided is, as a radioactive halogen labeling precursor compound that is highly reactive and stable, a compound represented by the following general formula (II):

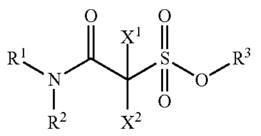

(II)

wherein $R^1$ and $R^2$ each independently represent an alkyl group having 5 to 20 carbon atoms, $X^1$ and $X^2$ each independently represent a halogen atom, and $R^3$ represents a monovalent group derived from a sugar, or the like.

10 Claims, 1 Drawing Sheet

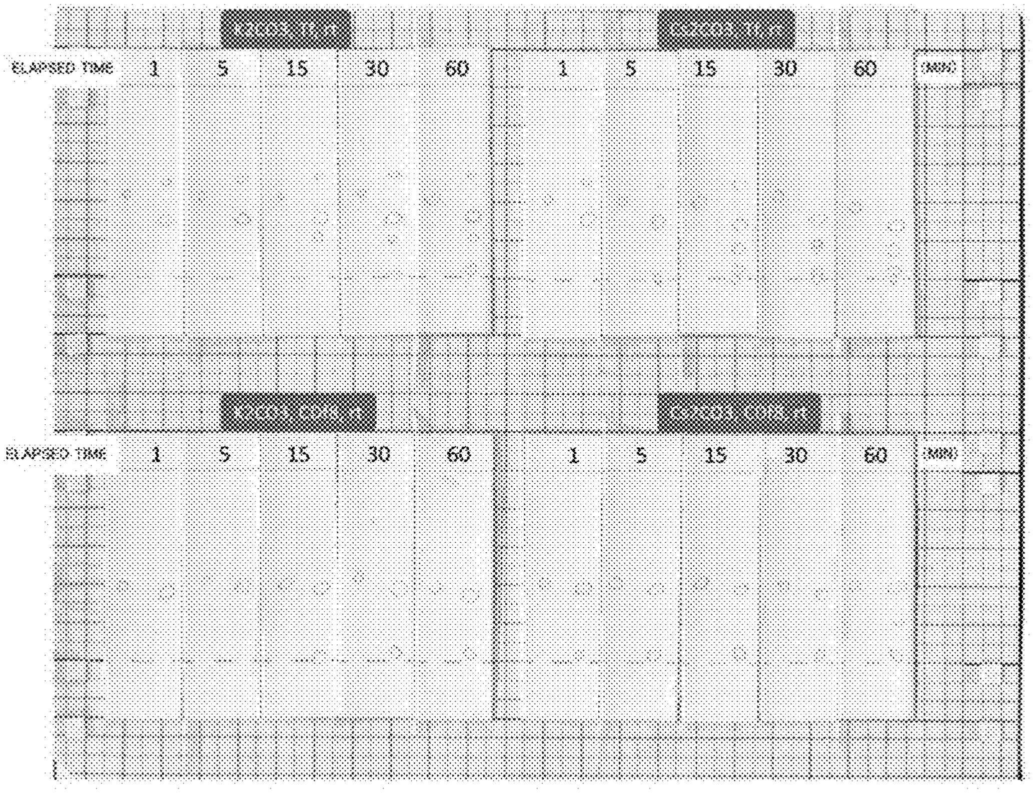
ELAPSED TIME
1
5
15
30
60
1
5
15
30
60
(MIN)
ELAPSED TIME
1
5
15
30
60
1
5
15
30
60
(MIN)

RADIOACTIVE HALOGEN LABELING PRECURSOR COMPOUND

TECHNICAL FIELD

The present invention relates to a radioactive halogen labeling precursor compound, a compound used in the production of this precursor compound, and a method for producing a radioactive halogen-labeled compound from this precursor compound.

BACKGROUND ART

Labeling reactions with radioactive halogens such as radioactive fluorine are often performed by synthesizing a compound with a leaving group bound to the halogen labeling site of a target substrate as a labeling precursor compound and then binding radioactive halogen to this labeling precursor compound. Here, the structure of the leaving group in the labeling precursor compound greatly affects the reactivity of the labeling reaction. As such leaving group, a trifluoromethanesulfonyloxy group, a benzenesulfonyloxy group, and the like are used.

Recently, the present inventor has developed and filed a patent application for a radioactive fluorine labeling precursor compound containing as a leaving group a benzenesulfonyloxy group to which a hydrophobic amide tag has been introduced (Patent Literatures 1 and 2). Since this precursor compound contains a hydrophobic moiety, the labeled compound of interest can be separated from the unreacted precursor compound advantageously by a simple method after the reaction is completed.

CITATION LIST

Patent Literature

[Patent Literature 1] International Publication No. WO 2018/164043

[Patent Literature 2] Japanese Patent Laid-Open No. 2017-52713

SUMMARY OF INVENTION

Technical Problem

To efficiently perform a labeling reaction with a radioactive halogen, it is necessary to use a highly reactive labeling precursor compound. However, even if the reactivity is high, the efficiency of the labeling reaction will not improve with a labeling precursor compound that is easily decomposed. The present invention has been made based on such technical background, and aims to provide a radioactive halogen labeling precursor compound that is highly reactive and stable.

Solution to Problem

As a result of extensive studies to solve the above problem, the present inventor has found that a radioactive halogen labeling precursor compound containing as a leaving group a trifluoromethanesulfonyloxy group to which a hydrophobic amide tag has been introduced has high reactivity and stability, and thereby completed the present invention.

That is, the present invention provides the following (1) to (17).

(1) A compound represented by the following general formula (I):

[Formula 1]

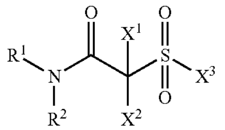

(I)

wherein $R^1$ and $R^2$ each independently represent an alkyl group having 5 to 20 carbon atoms, $X^1$ and $X^2$ each independently represent a halogen atom, and $X^3$ represents a halogen atom.

(2) The compound according to (1), wherein $R^1$ and $R^2$ in the general formula (I) are each an alkyl group having 7 to 11 carbon atoms.

(3) The compound according to (1) or (2), wherein $X^1$ and $X^2$ in the general formula (I) are each a fluorine atom or a chlorine atom.

(4) A compound represented by the following general formula (II):

[Formula 2]

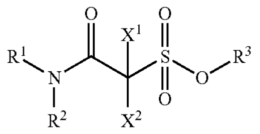

(II)

wherein $R^1$ and $R^2$ each independently represent an alkyl group having 5 to 20 carbon atoms, $X^1$ and $X^2$ each independently represent a halogen atom, and $R^3$ represents a monovalent group derived from a sugar, a monovalent group derived from a peptide, or a group represented by the following general formula (A) or (B):

[Formula 3]

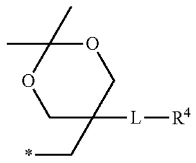

(A)

[Formula 4]

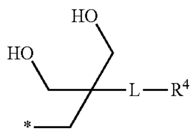

(B)

wherein L represents a divalent group that functions as a spacer, $R^4$ represents an aryl group optionally substituted with a substituent, a heteroaryl group optionally substituted with a substituent, or an aminocarbonyl group optionally protected by a protective group, and * represents a bonding site.

(5) The compound according to (4), wherein $R^1$ and $R^2$ in the general formula (II) are each an alkyl group having 7 to 11 carbon atoms.

(6) The compound according to (4) or (5), wherein $X^1$ and $X^2$ in the general formula (II) are each a fluorine atom or a chlorine atom.

(7) The compound according to any of (4) to (6), wherein L in the general formula (A) or (B) is an alkylene group, and one or more $—CH_2—$ of the alkylene group are optionally replaced with —O— or a phenylene group.

(8) The compound according to any of (4) to (7), wherein $R^4$ in the general formula (A) or (B) is a 4-[2,3-bis(tert-butoxycarbonyl)guanidinomethyl]phenyl group, a naphthalen-2-yl group, a 2-nitro-1H-imidazol-1-yl group, or an aminocarbonyl group protected by a tert-butoxycarbonyl group.

(9) A method for producing a radioactive halogen-labeled compound represented by the following general formula (IIIa):

[Formula 5]

$$X^4—R^{3a} \qquad \text{(IIIa)}$$

wherein $X^4$ represents a radioactive halogen atom and $R^{3a}$ represents a monovalent group derived from a compound to be labeled with a radioactive halogen atom; the method comprising a step of reacting a labeling precursor compound represented by the following general formula (IIa):

[Formula 6]

(IIa)

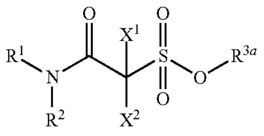

wherein $R^1$ and $R^2$ each independently represent an alkyl group having 5 to 20 carbon atoms, $X^1$ and $X^2$ each independently represent a halogen atom, and $R^{3a}$ has the same meaning as above, with a radioactive halide ion to obtain a radioactive halogen-labeled compound represented by the general formula (IIIa).

(10) The method according to (9), wherein $R^1$ and $R^2$ in the general formula (IIa) are each an alkyl group having 7 to 11 carbon atoms.

(11) The method according to (9) or (10), wherein $X^1$ and $X^2$ in the general formula (IIa) are each a fluorine atom or a chlorine atom.

(12) The method according to any of (9) to (11), wherein $R^{3a}$ in the general formulae (IIa) and (IIIa) is a monovalent group derived from a sugar, a monovalent group derived from a peptide, or a group represented by the following general formula (A) or (B):

[Formula 7]

(A)

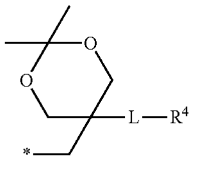

-continued

[Formula 8]

(B)

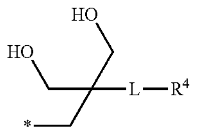

wherein L represents a divalent group that functions as a spacer, $R^4$ represents an aryl group optionally substituted with a substituent, a heteroaryl group optionally substituted with a substituent, or an aminocarbonyl group optionally protected by a protective group, and * represents a bonding site.

(13) The compound according to (12), wherein L in the general formula (A) or (B) is an alkylene group, and one or more $—CH_2—$ of the alkylene group are optionally replaced with —O— or a phenylene group.

(14) The compound according to (12) or (13), wherein $R^4$ in the general formula (A) or (B) is a 4-[2,3-bis(tert-butoxycarbonyl)guanidinomethyl]phenyl group, a naphthalen-2-yl group, a 2-nitro-1H-imidazol-1-yl group, or an aminocarbonyl group protected by a tert-butoxycarbonyl group.

(15) The method according to any of (9) to (14), wherein $X^4$ in the general formula (IIIa) is $^{211}At$.

(16) A reagent for producing a labeling precursor compound, containing the compound according to any of (1) to (3).

(17) A labeling precursor reagent for a radioactive halogen-labeled compound, containing the compound according to any of (4) to (8).

The present application claims priority to Japanese Patent Application No. 2021-006394, the contents of the specification and/or drawings of which are incorporated herein.

Advantageous Effects of Invention

The present invention provides a novel radioactive halogen labeling precursor compound. This precursor compound is highly reactive and stable, allowing efficient production of a radioactive halogen-labeled compound.

BRIEF DESCRIPTION OF DRAWINGS

FIG. 1 Photograph of TLC of the reaction solution (left lane: sample (iodine-substituted form of C), right lane: reaction solution).

DESCRIPTION OF EMBODIMENTS

The following describes in detail the present invention.

In the present invention, the "halogen atom" is, for example, a fluorine atom, a chlorine atom, a bromine atom, an iodine atom, or an astatine atom.

In the present invention, the "radioactive halogen atom" is, for example, $^{18}F$, $^{75}Br$, $^{76}Br$, $^{77}Br$, $^{82}Br$, $^{123}I$, $^{124}I$, $^{125}I$, $^{131}I$, $^{133}I$, $^{209}At$, $^{210}At$, or $^{211}At$.

In the present invention, the "radioactive halide ion" is, for example, $^{18}F^-$, $^{75}Br^-$, $^{76}Br^-$, $^{77}Br^-$, $^{82}Br^-$, $^{123}I$, $^{124}I^-$, $^{125}I^-$, $^{131}I^-$, $^{133}I^-$, $^{209}At^-$, $^{210}At^-$, or $^{211}At^-$.

In the present invention, the "alkyl group having 5 to 20 carbon atoms" is a linear or branched alkyl group having 5 or more and 20 or less carbon atoms, and is, for example, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, or an icosyl group.

In the present invention, the "alkyl group having 7 to 11 carbon atoms" is a linear or branched alkyl group having 7 or more and 11 or less carbon atoms, and is, for example, a heptyl group, an octyl group, a nonyl group, a decyl group, or an undecyl group.

In the present invention, the "aryl group" is, for example, a phenyl group, a naphthalen-1-yl group, or a naphthalen-2-yl group.

In the present invention, the "heteroaryl group" is, for example, a pyridin-2-yl group, a pyridin-3-yl group, a pyridin-4-yl group, a pyrimidin-2-yl group, a pyrimidin-4-yl group, a pyrimidin-5-yl group, a furan-2-yl group, a furan-3-yl group, a thiophen-2-yl group, a thiophen-3-yl group, an imidazol-1-yl group, an imidazol-2-yl group, an imidazol-4-yl group, or an imidazol-5-yl group.

In the present invention, the "protective group" of an aminocarbonyl group is, for example, a tert-butoxycarbonyl group (Boc), a benzyloxycarbonyl group, a 9-fluorenylmethyloxycarbonyl group, a 2,2,2-trichloroethoxycarbonyl group, an allyloxycarbonyl group, a trifluoroacetyl group, a phthaloyl group, a p-toluenesulfonyl group, or a 2-nitrobenzenesulfonyl group.

In the general formulae (I), (II), and (IIa), $R^1$ and $R^2$ each independently represent an alkyl group having 5 to 20 carbon atoms. $R^1$ and $R^2$ may be different groups, but are preferably the same group. $R^1$ and $R^2$ can be any of the groups mentioned above, but are each preferably an alkyl group having 7 to 11 carbon atoms, and more preferably an alkyl group having 7 or 11 carbon atoms.

In the general formulae (I), (II), and (IIa), $X^1$ and $X^2$ each independently represent a halogen atom. $X^1$ and $X^2$ may be different atoms, but are preferably the same atom. $X^1$ and $X^2$ can be any halogen atoms, but are each preferably a fluorine atom or a chlorine atom, and more preferably a fluorine atom.

In the general formula (I), $X^3$ represents a halogen atom. $X^3$ can be any halogen atom, but is preferably a fluorine atom.

In the general formula (II), $R^3$ represents a monovalent group derived from a sugar, or a monovalent group derived from a peptide. Here, a "monovalent group derived from a sugar" means, for example, a monovalent group obtained by removing one hydrogen atom in a sugar molecule, and a "monovalent group derived from a peptide" means, for example, a monovalent group obtained by removing one hydrogen atom in a peptide molecule. The hydrogen atom to be removed is, for example, a hydrogen atom in a hydroxy group contained in the sugar and peptide molecules. The type of sugar or peptide is not particularly limited, but one having the property of accumulating in specific organs and tissues in the body (such as cancer tissue) is preferred.

$R^3$ in the general formula (II) may represent a group represented by the following general formula (A) or (B):

[Formula 9]

(A)

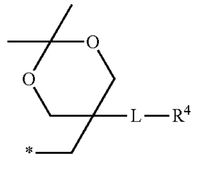

-continued

[Formula 10]

(B)

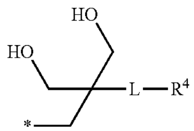

In the general formulae (A) and (B), L represents a divalent group that functions as a spacer. L may be a group having an aromatic ring, as long as it is a group that functions as a spacer. Specific examples of L include an alkylene group. However, one or more $—CH_2—$ of the alkylene group are optionally replaced with —O— or a phenylene group. Here, the phenylene group may be an o-phenylene group, a m-phenylene group, or a p-phenylene group. L can be any of the groups mentioned above, but is preferably $—CH_2—O—$, $—CH_2—O—CH_2—$, or $—CH_2—$. The number of carbon atoms of the alkylene group is not particularly limited, but is preferably 1 to 7, and more preferably 1 to 3. If $—CH_2—$ is replaced with —O— or a phenylene group, the —O— or phenylene group is also included in the "number of carbon atoms of the alkylene group" mentioned above as one carbon atom.

In the general formulae (A) and (B), $R^4$ represents an aryl group optionally substituted with a substituent, a heteroaryl group optionally substituted with a substituent, or an aminocarbonyl group optionally protected by a protective group. Here, the aryl group is not particularly limited, but a phenyl group or a naphthalen-2-yl group is preferred. Here, the heteroaryl group is not particularly limited, but an imidazol-1-yl group is preferred. The substituent is also not particularly limited, but a nitro group, a 2,3-bis(tert-butoxycarbonyl)guanidinomethyl group, a sulfo group and a fluorine atom are preferred, and a nitro group and a 2,3-bis(tert-butoxycarbonyl)guanidinomethyl group are more preferred. The protective group of the aminocarbonyl group is not particularly limited, but a tert-butoxycarbonyl group is preferred. $R^4$ can be any of the groups mentioned above, but is preferably a 4-[2,3-bis(tert-butoxycarbonyl)guanidinomethyl]phenyl group, a naphthalen-2-yl group, or a 2-nitro-1H-imidazol-1-yl group. When $R^4$ is an aminocarbonyl group optionally protected by a protective group, a functional moiety having an amino group can be easily bound thereto, and therefore when such functional moiety is to be bound, $R^4$ is preferably an aminocarbonyl group optionally protected by a protective group, e.g., an aminocarbonyl group protected by a tert-butoxycarbonyl group.

$R^{3a}$ in the general formulae (IIa) and (IIIa) represents a monovalent group derived from a compound to be labeled with a radioactive halogen atom. Here, the "monovalent group derived from a compound to be labeled with a radioactive halogen atom" means, for example, a monovalent group obtained by removing one hydrogen atom in the molecule of the compound, where the hydrogen atom to be removed is, for example, a hydrogen atom in a hydroxy group contained in the molecule of the compound. The monovalent group derived from a compound to be labeled with a radioactive halogen atom may be any group. Since the compound labeled with a radioactive halogen atom will be used as a radioactive drug (e.g., PET reagent), the part of the compound used as a radioactive drug other than the radioactive halogen atom may be a monovalent group derived from the compound to be labeled with a radioactive halogen atom. Since such part other than the radioactive halogen atom often has the property of accumulating in specific organs and tissues in the body (such as cancer tissue), such part may be a monovalent group derived from the compound to be labeled with a radioactive halogen atom. Furthermore, since such part other than the radioactive halogen atom often has the property of stabilizing the radioactive halogen atom in the body (e.g., the structure described in International Publication No. WO 2019/151384), such part may be a monovalent group derived from the compound to be labeled with a radioactive halogen atom. Specific examples of the monovalent group derived from the compound to be labeled with a radioactive halogen atom include the groups listed as examples of $R^3$ above.

$X^4$ in the general formula (IIIa) represents a radioactive halogen atom. $X^4$ can be any radioactive halogen atom, but is preferably $^{18}F$ or $^{211}At$, and more preferably $^{211}At$.

The compound represented by the general formula (I) can be used as a reagent for producing a labeling precursor compound, i.e., a starting material reagent for producing the compound represented by the general formula (II). The reagent for producing a labeling precursor compound usually consists solely of the compound represented by the general formula (I), but may also contain other substances. The compound represented by the general formula (I) can be produced according to the production method described in Example 1, in which 2,2-difluoro-2-(fluorosulfonyl)acetic acid and dioctylamine are used as starting materials, with modification and alteration as necessary.

The compound represented by the general formula (II) can be used as a labeling precursor reagent for a radioactive halogen-labeled compound. The labeling precursor reagent for a radioactive halogen-labeled compound usually consists solely of the compound represented by the general formula (II), but may also contain other substances. The compound represented by the general formula (II) can be produced, for example, by reacting the compound represented by the general formula (I) with a sugar, a peptide, or a compound containing a group represented by the general formula (A) or (B).

The compound represented by the general formula (II) has the following advantages as a precursor compound for a radioactive halogen-labeled compound.

1) It has a higher reactivity than conventional precursor compounds (e.g., precursor compounds containing a benzenesulfonyloxy group as a leaving group), enabling highly efficient radioactive halogenation.
2) It has a higher stability and is easier to handle than conventional precursor compounds (e.g., precursor compounds containing a trifluoromethanesulfonyloxy group as a leaving group), making it storable.
3) Since it contains a hydrophobic moiety, the labeled compound of interest can be separated from the unreacted precursor compound by a simple method after the reaction is completed.

The labeling precursor compound represented by the general formula (IIa) can be produced, for example, by reacting the compound represented by the general formula (I) with a compound having a hydroxy group.

The radioactive halogen-labeled compound represented by the general formula (IIIa) can be produced by reacting the labeling precursor compound represented by the general formula (IIa) with a radioactive halide ion. The radioactive halide ion used is not particularly limited, but is $^{18}F$- or $^{211}At$-, and more suitably $^{211}At$-. The reaction conditions can be appropriately set according to the type of precursor compound and radioactive halide ion. Those skilled in the art can easily select the appropriate reaction temperature, reaction time, concentration of each substance, and the like.

EXAMPLES

Hereafter, the present invention is described in further detail by way of Examples, but the present invention is not limited to these Examples.

[Example 1] Synthesis of Halogen-Labeled Compound

(1) Synthesis of 4-fluorosulfonylbenzoyl chloride (2)

[Formula 11]

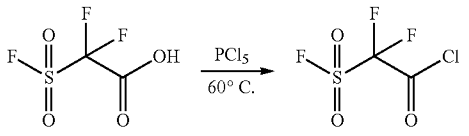

1 2

To a stirred solution of 2,2-difluoro-2-(fluorosulfonyl) acetic acid (1) (1.00 g, 5.62 mmol, 1.00 eq.) was added $PCl_3$ (1.31 g, 6.29 mmol, 1.12 eq.) at room temperature. After stirring at 60° C. for 3 hours, the reaction mixture was distilled to give 4-fluorosulfonylbenzoyl chloride (2) (1.03 g, 5.24 mmol, 93%).

(2) Synthesis of 2-(dioctylamino)-1,1-difluoro-2-oxoethane-1-sulfonyl fluoride (3)

[Formula 12]

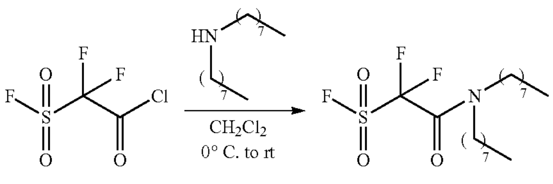

2 3

To a stirred solution of dioctylamine (4.40 mL, 14.6 mmol, 2.60 eq.) in $CH_2Cl_2$ (2.00 mL) was added a solution of 4-fluorosulfonylbenzoyl chloride (2) (1.03 g, 5.24 mmol, 93%) in $CH_2Cl_2$ (2.50 mL) at 0° C. After stirring at the same temperature for 3 hours, the reaction mixture was poured into $Et_2O$. The residue was filtered and concentrated in vacuo. The residue was purified by column chromatography on silica gel using toluene to give 2-(dioctylamino)-1,1-difluoro-2-oxoethane-1-sulfonyl fluoride (3) (534 mg, 1.33 mmol, 24%).

(3) Synthesis of 2-(didodecylamino)-1,1-difluoro-2-oxoethane-1-sulfonyl fluoride (4)

[Formula 13]

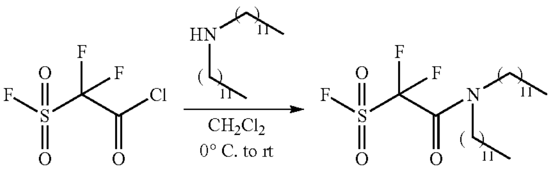

2

4

To a stirred solution of $NEt_3$ (3.52 mL, 25.3 mmol, 3.00 eq.) and didodecylamine (3.58 g, 10.1 mmol, 1.20 eq.) in $CH_2Cl_2$ (5.80 mL) was added a solution of 4-fluorosulfonylbenzoyl chloride (2) (1.03 g, 5.24 mmol, 93%) at −40° C. After stirring at the same temperature for 40 minutes, the reaction mixture was poured into $Et_2O$. The residue was filtered off and concentrated in vacuo. The residue was purified by column chromatography on silica gel using toluene to give 2-(didodecylamino)-1,1-difluoro-2-oxoethane-1-sulfonyl fluoride (4) (961 mg, 1.87 mmol, 22%).

(4) Synthesis of (E)-(5-((4-((2,3-bis(tert-butoxycarbonyl)guanidino)methyl)phenoxy)methyl)-2,2-dimethyl-1,3-dioxan-5-yl)methyl 2-(dioctylamino)-1,1-difluoro-2-oxoethane-1-sulfonate (6)

[Formula 14]

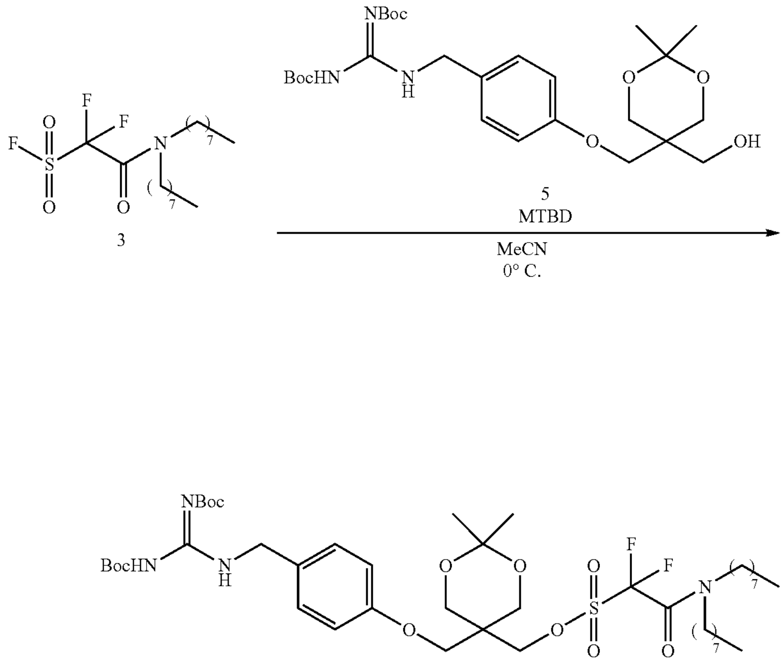

3

5

6

To a stirred solution of 2-(dioctylamino)-1,1-difluoro-2-oxoethane-1-sulfonyl fluoride (3) (164.9 mg, 0.414 mmol, 2.00 eq.) and (2,2-dimethyl-(E)-(5-(4-(2,3-bis(tert-(butoxycarbonyl)guanidino)methyl)phenoxy)-1,3-dioxan-5-yl) methanol (5) (108.3 mg, 0.207 mmol, 1.00 eq.) in $CH_3CN$ (0.951 mL) was added MTBD (89.7 μL, 0.621 mmol, 3.00 eq.) at 0° C. After stirring at the same temperature for 20 minutes, the reaction mixture was poured into an $NH_4Cl$ aqueous solution and the aqueous layer was extracted twice with EtOAc. The combined extracts were washed with brine, dried over $MgSO_4$, filtered, and concentrated in vacuo. The residue was purified by column chromatography on silica gel using hexane:EtOAc (80:20) to give (E)-(5-((4-((2,3-bis(tert-butoxycarbonyl)guanidino)methyl)phenoxy)methyl)-2,2-dimethyl-1,3-dioxan-5-yl)methyl 2-(dioctylamino)-1,1-difluoro-2-oxoethane-1-sulfonate (6) (47.4 mg, 0.0524 mmol, 25%).

(5) Synthesis of (E)-(5-(4-((2,3-bis(tert-butoxycarbonyl)guanidino)methyl)phenoxy)methyl)-2,2-dimethyl-1,3-dioxan-5-yl)methyl-2-(didodecylamino)-1,1-difluoro-2-oxoethane-1-sulfonate (7)

[Formula 15]

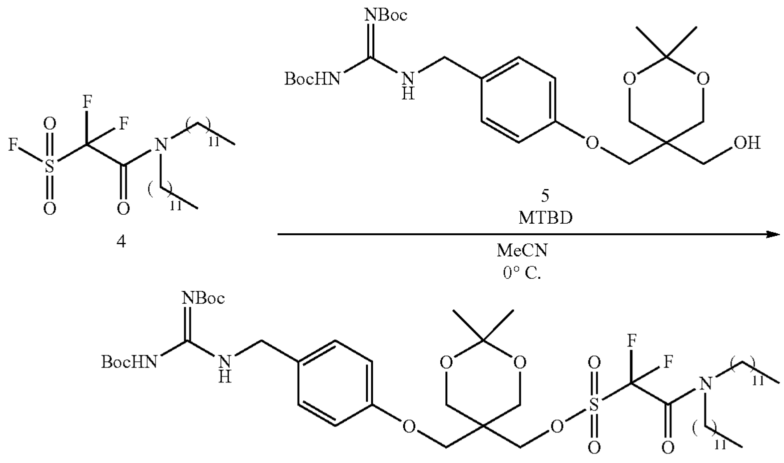

7

To a stirred solution of 2-(didodecylamino)-1,1-difluoro-2-oxoethane-1-sulfonyl fluoride (4) (103.5 mg, 0.202 mmol, 1.60 eq.) and (2,2-dimethyl-(E)-(5-(4-(2,3-bis(tert-(butoxycarbonyl)guanidino)methyl)phenoxy)-1,3-dioxan-5-yl)methanol (5) (66.1 mg, 0.207 mmol, 1.00 eq.) in $CH_3CN$ (0.624 mL) was added MTBD (54.7 μL, 0.379 mmol, 3.00 eq.) at 0° C. After stirring at the same temperature for 20 minutes, the reaction mixture was poured into an $NH_4Cl$ aqueous solution and the aqueous layer was extracted twice with EtOAc. The combined extracts were washed with brine, dried over $MgSO_4$, filtered, and concentrated in vacuo. The residue was purified by column chromatography on silica gel with hexane:EtOAc (80:20) to give (E)-(5-(4-((2,3-bis(tert-butoxycarbonyl)guanidino)methyl)phenoxy)methyl)-2,2-dimethyl-1,3-dioxan-5-yl)methyl-2-(didodecylamino)-1,1-difluoro-2-oxoethane-1-sulfonate (7) (109.8 mg, 0.108 mmol, 86%).

(6) Synthesis of 5-iodomethyl-(E)-(5-((4-((2,3-bis(tert-butoxycarbonyl)guanidino)methyl)phenoxy)methyl)-2,2-dimethyl-1,3-dioxane (8)

[Formula 16]

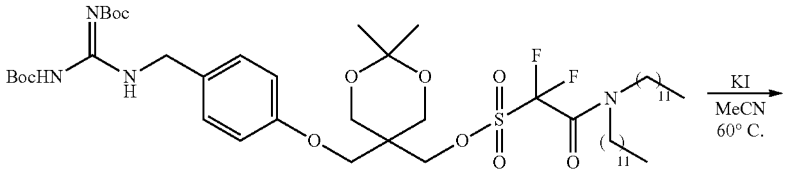

7

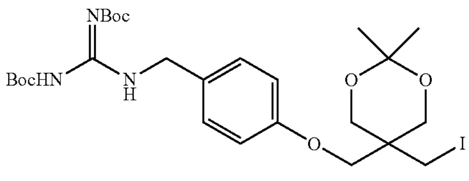

8

To a stirred solution of (E)-(5-((4-((2,3-bis(tert-butoxycarbonyl)guanidino)methyl)phenoxy)methyl)-2,2-dimethyl-1,3-dioxan-5-yl)methyl 2-(didodecylamino)-1,1-difluoro-2-oxoethane-1-sulfonate (7) (50.6 mg, 0.0497 mmol, 1.00 eq.) in DMF (0.280 mL) was added potassium iodine (18.3 mg, 0.0995 mmol, 2.00 eq.) at 60° C. After stirring at the same temperature for 1.5 hours, the reaction mixture was poured into a 10% $Na_2SO_4$ aqueous solution. The aqueous layer was extracted twice with EtOAc. The combined extracts were washed with brine, dried over $MgSO_4$, filtered, and concentrated in vacuo. The residue was purified by column chromatography on silica gel using hexane:EtOAc (80:20) to give 5-iodomethyl-(E)-(5-((4-((2,3-bis(tert-butoxycarbonyl)guanidino)methyl)phenoxy)methyl)-2,2-dimethyl-1,3-dioxane (8) (28.3 mg, 0.0447 mmol, 90%).

(7) Synthesis of 1-(4-(3-hydroxy-2-(hydroxymethyl)-2-(iodomethyl)propoxy)benzyl) guanidine (9)

[Formula 17]

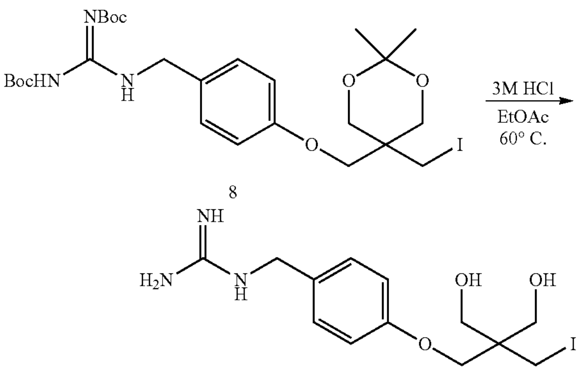

8

9

To a stirred solution of (E)-(5-((4-((2,3-bis(tert-butoxycarbonyl)guanidino)methyl)phenoxy)methyl)-2,2-dimethyl-1,3-dioxan-5-yl)methyl 2-(didodecylamino)-1,1-difluoro-2-oxoethane-1-sulfonate (8) (12.0.0 mg. 0189 mmol, 1.00 eq.) in EtOAc (0.150 mL) was added 3M HCl (0.150 mL) at 60° C. After stirring at the same temperature for 45 minutes, the reaction mixture was poured into MeOH and concentrated in vacuo. The residue was purified by Bond Elut with water to give 1-(4-(3-hydroxy-2-(hydroxymethyl)-2-(iodomethyl)propoxy)benzyl)guanidine (9) (4.9 mg, 0.00120 mmol, 66%).

(8) Synthesis of (2,2-dimethyl-5-((naphthalen-2-ylmethoxy)methyl)-1,3-dioxan-5-yl)methyl 2-(dioctylamino)-1,1-difluoro-2-oxoethane-1-sulfonate (11)

[Formula 18]

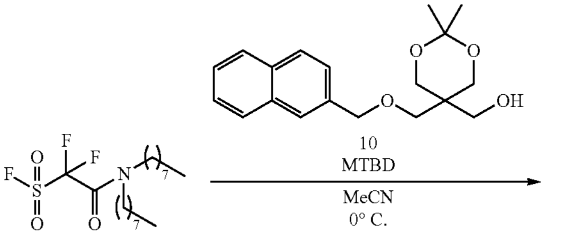

3

-continued

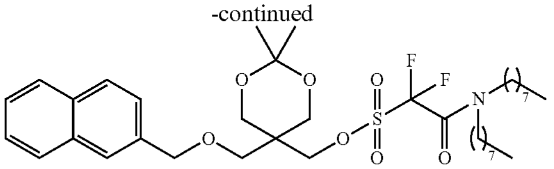

11

To a stirred solution of 2-(dioctylamino)-1,1-difluoro-2-oxoethane-1-sulfonyl fluoride (3) (328 mg, 0.818 mmol, 2.00 eq.) and (2,2-dimethyl-5-((naphthalen-2-ylmethoxy)methyl)-1,3-dioxan-5-yl)methanol (10) (138 mg, 0.435 mmol, 1.00 eq.) in $CH_3CN$ (0.951 mL) was added MTBD (189 µL, 1.31 mmol, 3.00 eq.) at 0° C. After stirring at the same temperature for 20 minutes, the reaction mixture was poured into an $NH_4Cl$ aqueous solution and the aqueous layer was extracted twice with EtOAc. The combined extracts were washed with brine, dried over $MgSO_4$, filtered, and concentrated in vacuo. The residue was purified by column chromatography on silica gel using hexane:EtOAc (80:20) to give (2,2-dimethyl-5-((naphthalen-2-ylmethoxy)methyl)-1,3-dioxan-5-yl)methyl 2-(dioctylamino)-1,1-difluoro-2-oxoethane-1-sulfonate (11) (23.1 mg, 0.0330 mmol, 8%).

(9) Synthesis of (2,2-dimethyl-5-((naphthalen-2-ylmethoxy)methyl)-1,3-dioxan-5-yl)methyl 2-(didodecylamino)-1,1-difluoro-2-oxoethane-1-sulfonate

[Formula 19]

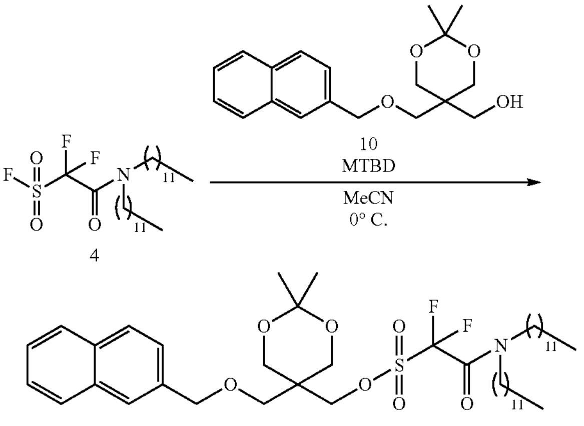

4

12

To a stirred solution of 2-(didodecylamino)-1,1-difluoro-2-oxoethane-1-sulfonyl fluoride (4) (103.2 mg, 0.201 mmol, 1.50 eq.) and (2,2-dimethyl-5-((naphthalen-2-ylmethoxy)methyl)-1,3-dioxan-5-yl)methanol (10) (43.0 mg, 0.134 mmol, 1.00 eq.) in $CH_3CN$ (0.624 mL) was added MTBD (38.7 µL, 0.268 mmol, 2.00 eq.) at 0° C. After stirring at the same temperature for 20 minutes, the reaction mixture was poured into an $NH_4Cl$ aqueous solution and the aqueous layer was extracted twice with EtOAc. The combined extracts were washed with brine, dried over $MgSO_4$, filtered, and concentrated in vacuo. The residue was purified by column chromatography on silica gel using toluene:EtOAc (90:10) to give (2,2-dimethyl-5-((naphthalen-2-ylmethoxy)

methyl)-1,3-dioxan-5-yl)methyl 2-(didodecylamino)-1,1-difluoro-2-oxoethane-1-sulfonate (12) (84.2 mg, 0.104 mmol, 78%).

(10) Synthesis of 5-iodomethyl-5-((naphthalen-2-ylmethoxy)methyl)-2,2-dimethyl-1,3-dioxane (14)

[Formula 20]

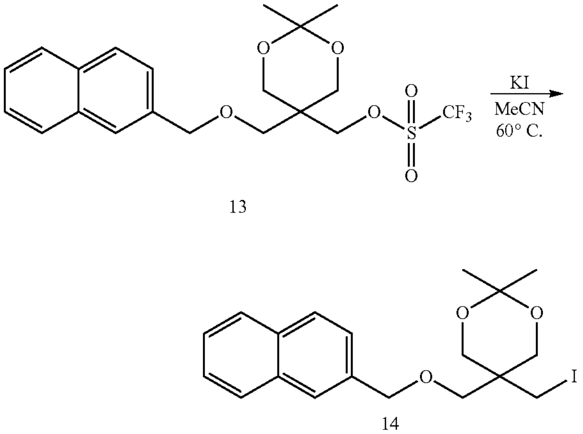

13
14

To a stirred solution of methyl (2,2-dimethyl-5-((naphthalen-2-ylmethoxy)methyl)-1,3-dioxan-5-yl)trifluoromethanesulfonate (13) (11.0 mg, 0.0245 mmol, 1.00 eq.) in $CH_3CN$ (0.350 mL) was added potassium iodine (5.20 mg, 0.0310 mmol, 1.30 eq.) at room temperature. After stirring at 60° C. for 30 minutes, the reaction mixture was poured into a 10% $Na_2SO_3$ aqueous solution and the aqueous layer was extracted twice with EtOAc. The combined extracts were washed with brine, dried over $MgSO_4$, filtered, and concentrated in vacuo. The residue was purified by column chromatography on silica gel using hexane:EtOAc (80:20) to give 5-iodomethyl-5-((naphthalen-2-ylmethoxy)methyl)-2,2-dimethyl-1,3-dioxane (14) (7.8 mg, 0.0180 mmol, 75%).

(11) Synthesis of (2,2-dimethyl-5-((naphthalen-2-ylmethoxy)methyl)-1,3-dioxan-5-yl)methyl 2-(dioctylamino)-1,1-difluoro-2-oxoethane-1-sulfonate (16)

[Formula 21]

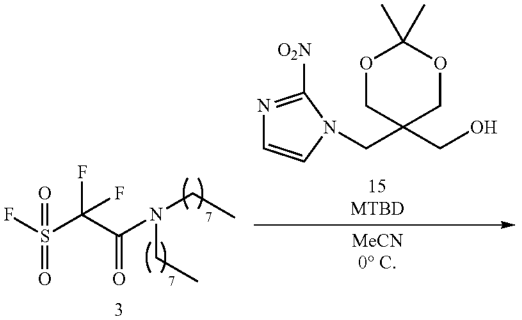

15
3

-continued

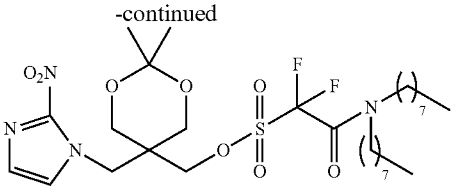
16

To a stirred solution of 2-(dioctylamino)-1,1-difluoro-2-oxoethane-1-sulfonyl fluoride (3) (118 mg, 0.294 mmol, 1.50 eq.) and (2,2-dimethyl-5-((2-nitro-1H-imidazol-1-yl)methyl)-1,3-dioxan-5-yl)methanol (15) (52.6 mg, 0.194 mmol, 1.00 eq.) in $CH_3CN$ (0.725 mL) was added MTBD (56.6 μL, 0.392 mmol, 2.00 eq.) at 0° C. After stirring at the same temperature for 20 minutes, the reaction mixture was poured into an $NH_4Cl$ aqueous solution and the aqueous layer was extracted twice with EtOAc. The combined extracts were washed with brine, dried over $MgSO_4$, filtered, and concentrated in vacuo. The residue was purified by column chromatography on silica gel using hexane:EtOAc (80:20) to give (2,2-dimethyl-5-((naphthalen-2-ylmethoxy)methyl)-1,3-dioxan-5-yl)methyl 2-(dioctylamino)-1,1-difluoro-2-oxoethane-1-sulfonate (16) (55.9 mg, 0.0856 mmol, 44%).

(12) Synthesis of (2,2-dimethyl-5-((naphthalen-2-ylmethoxy)methyl)-1,3-dioxan-5-yl)methyl 2-(didodecylamino)-1,1-difluoro-2-oxoethane-1-sulfonate

[Formula 22]

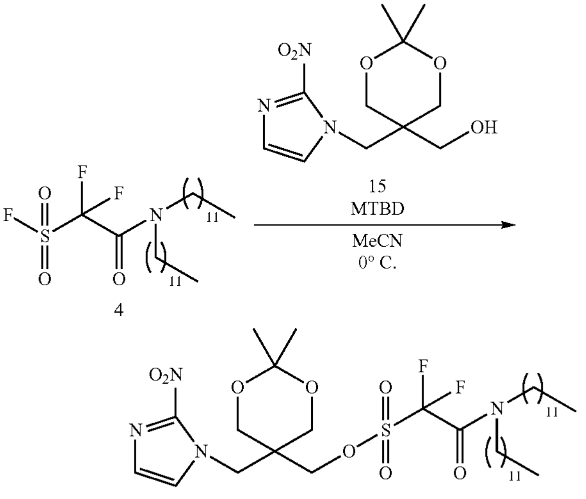

15
4
17

To a stirred solution of 2-(didodecylamino)-1,1-difluoro-2-oxoethane-1-sulfonyl fluoride (4) (124 mg, 0.241 mmol, 1.50 eq.) and (2,2-dimethyl-5-((2-nitro-1H-imidazol-1-yl)methyl)-1,3-dioxan-5-yl)methanol (15) (43.7 mg, 0.161 mmol, 1.00 eq.) in $CH_3CN$ (0.702 mL) was added MTBD (46.4 μL, 0.321 mmol, 2.00 eq.) at 0° C. After stirring at the same temperature for 20 minutes, the reaction mixture was poured into an $NH_4Cl$ aqueous solution and the aqueous layer was extracted twice with EtOAc. The combined extracts were washed with brine, dried over $MgSO_4$, filtered, and concentrated in vacuo. The residue was purified by column chromatography on silica gel using toluene:EtOAc (90:10) to give (2,2-dimethyl-5-((2-nitro-1H-imidazol-1-yl) methyl)-1,3-dioxan-5-yl)methyl 2-(didodecylamino)-1,1-difluoro-2-oxoethane-1-sulfonate (17) (73.3 mg, 0.0958 mmol, 60%).

(13) Synthesis of 5-iodomethyl-5-((naphthalen-2-ylmethoxy)methyl)-2,2-dimethyl-1,3-dioxane (19)

[Formula 23]

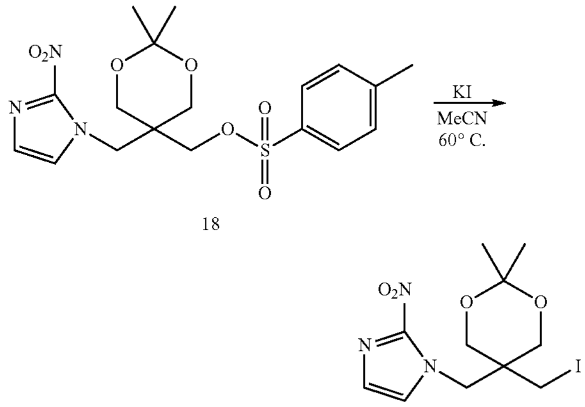

18

19

To a stirred solution of (2,2-dimethyl-5-((2-nitro-1H-imidazol-1-yl)methyl)-1,3-dioxan-5-yl)methyl 4-methylbenzenesulfonate (18) (48.8 mg, 0.115 mmol, 1.00 eq.) in $CH_3CN$ (0.651 mL) was added potassium iodine (86.0 mg, 0.518 mmol, 4.50 eq.) at room temperature. After stirring at 60° C. for 30 minutes, the reaction mixture was poured into a 10% $Na_2SO_3$ aqueous solution and the aqueous layer was extracted twice with EtOAc. The combined extracts were washed with brine, dried over $MgSO_4$, filtered, and concentrated in vacuo. The residue was purified by column chromatography on silica gel using hexane:EtOAc (50:50) to give 5-iodomethyl-5-((naphthalen-2-ylmethoxy)methyl)-2, 2-dimethyl-1,3-dioxane (19) (24.2 mg, 0.0635 mmol, 55%).

(14) Synthesis of 2-(iodomethyl)-2-((2-nitro-1H-imidazol-1-yl)methyl)propane-1,3-diol (20)

[Formula 24]

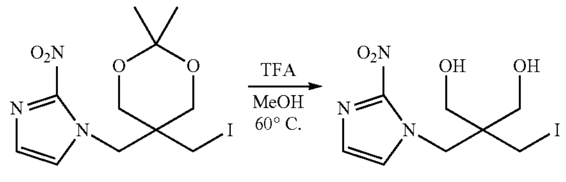

19 20

To a stirred solution of 1-((5-(iodomethyl)-2,2-dimethyl-1,3-dioxan-5-yl)methyl)-2-nitro-1H-imidazole (19) (10.0 mg, 0.0262 mmol, 1.00 eq.) in MeOH (0.262 mL) was added TFA (0.606 μL) at 0° C. After stirring at 60° C. for 1.5 hours, the reaction mixture was poured into toluene and then concentrated in vacuo. The residue was purified by column chromatography on silica gel using chloroform:MeOH (90:

10) to give 2-(iodomethyl)-2-((2-nitro-1H-imidazol-1-yl) methyl)propane-1,3-diol (20) (8.9 mg, 0.0260 mmol, 99%).

[Example 2] Synthesis of Halogen-Labeled Precursor Compound (1) Synthesis of (5-(benzyloxymethyl)-2,2-dimethyl-1,3-dioxiran-5-yl) methanol

[Formula 25]

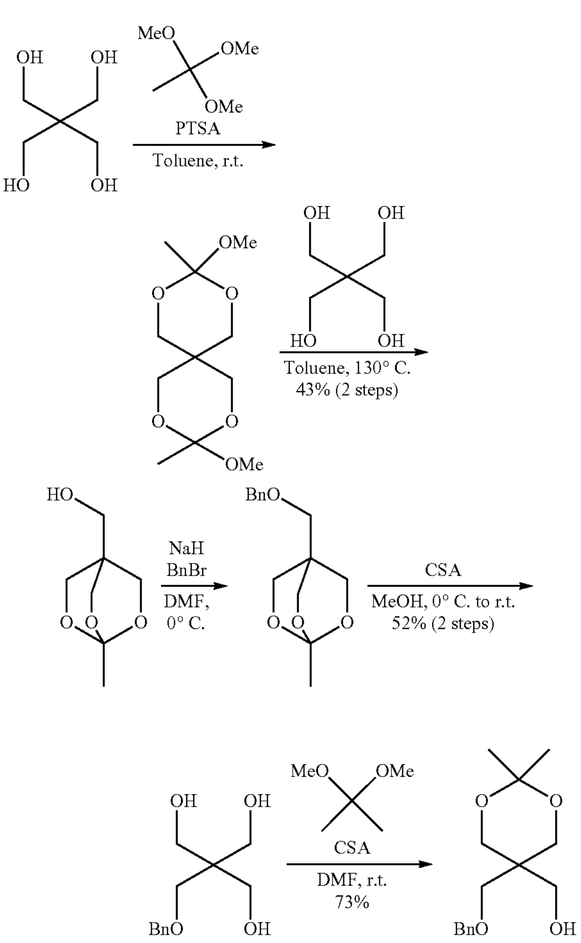

(1-1) Synthesis of 4-(hydroxymethyl)-1-methyl-2,6,7-trioxabicyclo[2.2.2]octane

A solution of pentaerythritol (10.0 g, 73.4 mmol), 1,1,1-trimethoxyethane (28.7 mL, 220 mmol, 3.00 eq.) and p-toluenesulfonic acid monohydrate (140 mg, 0.734 mmol, 0.01 eq.) in toluene (36.5 mL) was reacted at 0° C. for 12 hours. Then, pentaerythritol (10.0 g, 73.4 mmol, 1.00 eq.) was added thereto and reacted at 130° C. for 3 hours, followed by the addition of triethylamine (1.0 mL) for neutralization. The product was concentrated under reduced pressure and recrystallized using toluene, diethyl ether and hexane to give the title compound (4.98 g, 31.1 mmol, 43%) as white crystals.

[Formula 26]

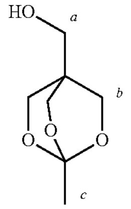

$^1H$ NMR (400 MHz, $CDCl_3$) δ 4.05 (s, 6H, H-b), 3.46 (s, 2H, H-a,), 1.45 (s, 3H, H-c);

(1-2) Synthesis of 2-(benzyloxymethyl)-2-(hydroxymethyl)propane-1,3-diol

Sodium hydride (3.17 g, 132 mmol, 2.12 eq.) was washed using dry hexane, then dry N,N-dimethylformamide (15.5 mL) was added thereto, followed by the addition of a solution of 4-(hydroxymethyl)-1-methyl-2,6,7-trioxabicyclo[2.2.2]octane in dry N,N-dimethylformamide (15.5 mL) at 0° C. After stirring at room temperature for 1 hour, benzyl bromide (11.1 mL, 93.7 mmol, 1.50 eq.) was added at 0° C. After reacting at room temperature for 2 hours, methanol (5.0 ml) was added, and then the mixture was poured into ethyl acetate and water. After extracting the aqueous layer with ethyl acetate, the organic layer was washed with saturated brine and dried using magnesium sulfate. The solution from which magnesium sulfate was removed by filtration was concentrated under reduced pressure. After diluting the obtained residue with methanol (100 mL), camphorsulfonic acid (1.45 g, 6.24 mmol, 0.01 eq.) was added and reacted at room temperature for 12 hours. After the reaction solution was emptied into water and washed with hexane/ethyl acetate=(9:1), the target product was extracted from the remaining aqueous layer using ethyl acetate. The organic layer was washed with saturated brine, and then dried using magnesium sulfate. After removing the magnesium sulfate by filtration, the obtained solution was concentrated to give the title compound (7.38 g, 32.6 mmol, 52%).

[Formula 27]

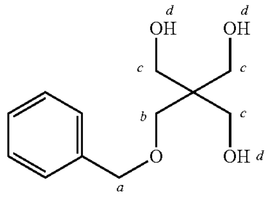

$^1H$ NMR (400 MHz, $CDCl_3$) δ 7.26-7.36 (m, 5H, H-aromatic), 4.48 (s, 2H, H-a), 3.68 (s, 6H, H-c), 3.47 (s, 2H, H-b), 2.17 (s, 3H, H-d);

(1-3) Synthesis of (5-(benzyloxymethyl)-2,2-dimethyl-1,3-dioxiran-5-yl)methanol

To a solution of 2-(benzyloxymethyl)-2-(hydroxymethyl)propane-1,3-diol (7.34 g, 32.4 mmol, 1.0 eq.) and camphorsulfonic acid (7.54 mg, 0.0324 mmol, 0.001 eq.) in N,N-dimethylformamide (16.2 mL), 2,2-dimethoxypropane (4.8 mL, 38.9 mmol, 1.20 eq.) was added at room temperature. The reaction solution was reacted at 60° C. for 40 minutes, then neutralized using triethylamine and poured into water and ethyl acetate. The aqueous layer was extracted using ethyl acetate, and the obtained organic layer was washed with saturated brine, then dried using magnesium sulfate. After removing the magnesium sulfate by filtration, the solution was concentrated under reduced pressure. The obtained residue was purified using silica gel column chromatography, then recrystallized using hexane and ethyl acetate to give the title compound (6.30 g, 23.6 mmol, 73%).

[Formula 28]

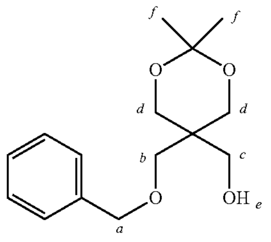

$^1H$ NMR (400 MHz, $CDCl_3$) δ 7.28-7.38 (m, 5H, H-aromatic), 4.54 (s, 2H, H-a), 3.73 (m, 4H, H-d), 3.68 (d, 2H, H-e, J=6.0 Hz), 3.58 (s, 2H, H-c), 2.35 (t, 1H, H-e, J=6.0 Hz), 1.41 (d, 6H, H-f, J=5.6 Hz);

(2) Synthesis of tert-butyl 2-((5-((benzyloxymethyl)-2,2-dimethyl-1,3-dioxan-5-yl) methoxy)acetate

[Formula 29]

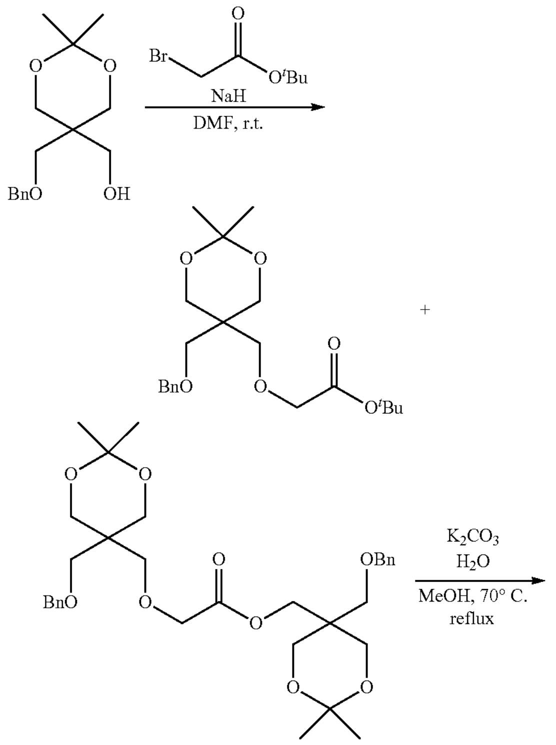

-continued

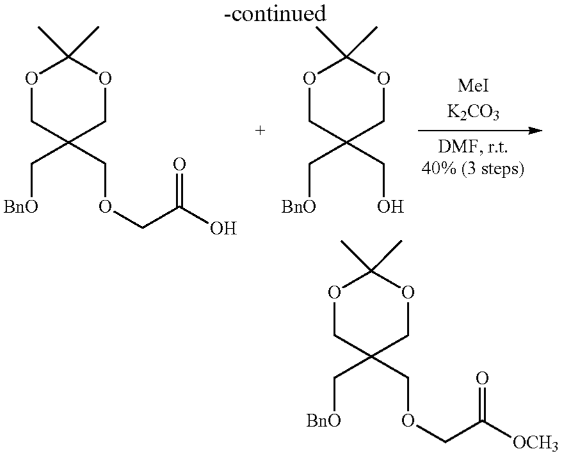

Sodium hydride (1.75 g, 43.7 mmol, 2.00 eq.) was washed with dry hexane, and then dry N,N-dimethylformamide (16.4 mL) was added. Next, tert-butyl 2-bromoacetate (4.81 mL, 32.8 mmol, 1.50 eq.) was added at 0° C. After reacting at room temperature for 1 hour, ethanol was added to stop the reaction, and then the mixture was poured into ethyl acetate and water. After extracting the aqueous layer using ethyl acetate, the organic layer was washed with saturated brine and dried using magnesium sulfate. After removing the magnesium sulfate by filtration, the solution was concentrated under reduced pressure. The obtained residue was diluted with methanol (42 mL), and then potassium carbonate (5.83 g, 42.2 mmol, 2.0 eq.) and water (0.761 mL, 42.2 mmol, 2.0 eq.) were added at 0° C. After reacting at room temperature for 2.5 hours, the reaction solution was concentrated under reduced pressure. The obtained residue was diluted with dry N,N-dimethylformamide (60 mL), and then potassium carbonate (11.7 g, 84.5 mmol, 4.0 eq.) and iodomethane (3.96 mL, 63.4 mmol, 3.0 eq.) were added. After reacting at room temperature for 2 hours, the reaction solution was poured into a saturated aqueous ammonium chloride solution. After extracting the aqueous layer with ethyl acetate, the organic layer was washed with saturated brine and dried using magnesium sulfate. After removing the magnesium sulfate by filtration, the solution was concentrated under reduced pressure. The obtained residue was purified by silica gel chromatography to give the title compound (2.84 g, 8.39 mmol, 40%).

[Formula 30]

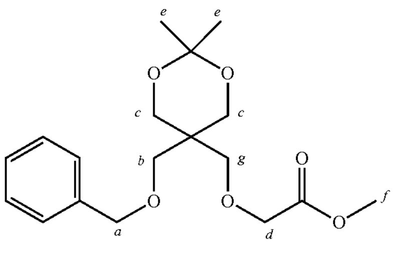

$^1$H NMR (400 MHz, $CDCl_3$) δ 7.26-7.36 (m, 5H, H-aromatic), 4.52 (s, 2H, H-a), 4.07 (s, 2H, H-d), 3.80 (s, 4H, H-c), 3.73 (s, 3H, H-f), 3.58 (s, 2H, H-b), 3.51 (s, 2H, H-g), 1.41 (d, 6H, H-e, J=4.4 Hz);

(3) Synthesis of 2-((5-((hydroxymethyl)-2,2-dimethyl-1,3-dioxan-5-yl)methoxy)acetamide

[Formula 31]

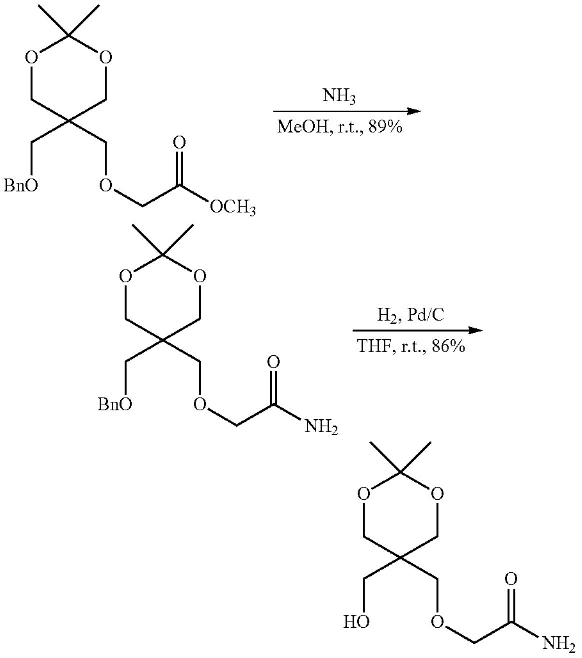

(3-1) Synthesis of 2-((5-((benzyloxymethyl)-2,2-dimethyl-1,3-dioxan-5-yl)methoxy)acetamide To a solution of tert-butyl 2-((5-((benzyloxymethyl)-2,2-dimethyl-1,3-dioxan-5-yl)methoxy)acetate (8.75 g, 25.9 mmol, 1.0 eq.) in methanol (13.5 mL), ammonia (13.5 mL) was added at −30° C. After sealing the tube, the mixture was reacted at room temperature for 12 hours. After opening the tube, the mixture was stirred at room temperature to remove ammonia, and then methanol was removed under reduced pressure. The obtained residue was purified using silica gel column chromatography to give the title compound (7.48 g, 23.1 mmol, 89%).

[Formula 32]

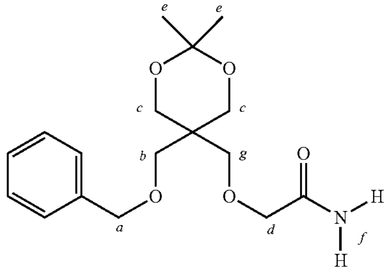

$^1$H NMR (400 MHz, $CDCl_3$) δ 7.28-7.38 (m, 5H, H-aromatic), 6.77 (br, 1H, N—H), 5.35 (br, 1H, N—H), 4.51 (s, 2H, H-a), 3.94 (s, 2H, H-d), 3.74 (m, 4H, H-c), 3.60 (s, 2H, H-b), 3.48 (s, 2H, H-g), 1.41 (d, 6H, H-e, J=6.4 Hz);

(3-2) Synthesis of 2-((5-((hydroxymethyl)-2,2-dimethyl-1,3-dioxan-5-yl)methoxy)acetamide To a suspension of Pd/C (6.93 g, 0.3 g/mmol, 10%) in tetrahydrofuran (348 mL) was added 2-((5-((benzyloxymethyl)-2,2-dimethyl-1,3-dioxan-5-yl)methoxy)acetamide (7.48 g, 23.1 mmol, 1.0 eq.). After placing the reaction vessel under a hydrogen atmosphere at normal pressure, the mixture was reacted at room temperature for 2 hours. After filtering the reaction solution, the filtrate was concentrated under reduced pressure. The obtained residue was purified using silica gel column chromatography to give the title compound (4.13 g, 17.7 mmol, 76%).

[Formula 33]

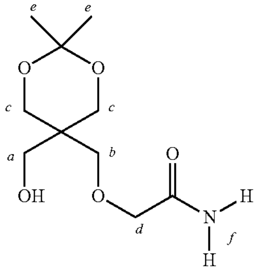

$^1$H NMR (400 MHz, $CDCl_3$) δ 6.76 (br, 1H, N—H), 5.41 (br, 1H, N—H), 4.01 (s, 2H, H-d), 3.74 (m, 4H, H-c), 3.70 (d, 2H, H-a, J=5.2 Hz), 3.64 (s, 2H, H-b), 1.42 (d, 6H, H-e, J=6.4 Hz);

(4) Synthesis of (5-((2-(bis(tert-butoxycarbonyl)amino)-2-oxoethyl)methyl)-2,2-dimethyl-1,3-dioxan-5-yl)methyl 2-(dioctylamino)-1,1-difluoro-2-oxoethane-1-sulfonate

[Formula 34]

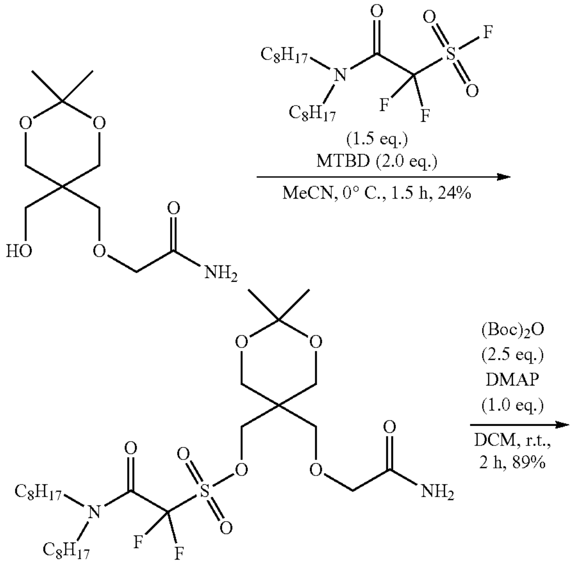

-continued

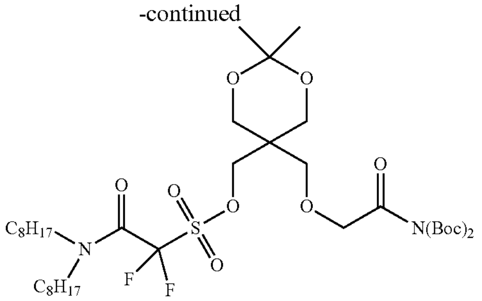

(4-1) Synthesis of (5-((2-amino-2-oxaethoxy)methyl)-2,2-dimethyl-1,3-oxiran-5-yl)methyl 2-(didioctylamino)-1,1-difluoro-2-oxaethane-1-sulfonate To a solution of 2-((5-(hydroxymethyl)-2,2-dimethyl-1,3-dioxiran-5-yl)methoxy)acetamide (100 mg, 429 μmol, 1.0 eq.) in dry acetonitrile (1.0 mL) was added a solution of 7-methyl-1,5,7-triazabicyclo[4.4.0]dec-5-ene (124 μL, 857 μmol, 2.0 eq.) and 2-(dioctylamino)-1,1-difluoro-2-oxaethane-1-sulfonyl fluoride (258 mg, 643 μmol, 1.5 eq.) in dry acetonitrile (1.0 mL) at 0° C. After reacting under ice cooling for 1.5 hours, the reaction solution was poured into ethyl acetate and water. After extracting the aqueous layer using ethyl acetate, the organic layer was washed with saturated brine and then dried using magnesium sulfate. After removing the magnesium sulfate by filtration, the filtrate was concentrated under reduced pressure. The residue was purified using silica gel column chromatography to give the title compound (63.5 mg, 103 μmol, 24%).

[Formula 35]

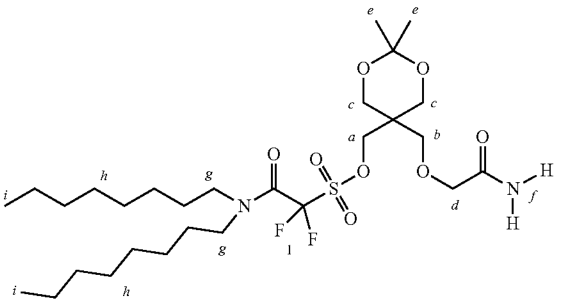

$^1$H NMR (400 MHz, $CDCl_3$) δ 6.71 (br, 1H, N—H), 5.49 (br, 1H, N—H), 4.61 (s, 2H, H-d), 4.00 (s, 2H, H-a), 3.75 (m, 4H, H-c), 3.57 (s, 2H, H-b), 3.36 (m, 4H, H-g), 1.42 (d, 6H, H-e, J=2.5 Hz), 1.27 (m, 24H, H-h), 0.881 (m, 6H, H-i); $^{19}$F NMR (400 MHz, $CDCl_3$) δ −98.0 (s, 2F, F-1)

(4-2) Synthesis of (5-((2-(bis(tert-butoxycarbonyl)amino)-2-oxoethyl)methyl)-2,2-dimethyl-1,3-dioxan-5-yl)methyl 2-(dioctylamino)-1,1-difluoro-2-oxoethane-1-sulfonate To a solution of (5-((2-amino-2-oxaethoxy)methyl)-2,2-dimethyl-1,3-oxiran-5-yl)methyl 2-(didioctylamino)-1,1-difluoro-2-oxaethane-1-sulfonate (40 mg, 65 μmol, 1.0 eq.) in dry dichloromethane (2.0 mL) were added a 30% 1,4-dioxane solution of di-tert-butyl bicarbonate (110 μL, 160 μmol, 2.5 eq.) and N,N-dimethylaminopyridine (7.9 mg, 65

μmol, 1.0 eq.) at 0° C. After reacting at room temperature for 2 hours, the mixture was poured into a mixed solution of ethyl acetate and water. The aqueous layer was extracted using ethyl acetate, and the organic layer was washed with saturated brine, then dried using magnesium sulfate. The filtrate from which magnesium sulfate was removed by filtration was concentrated under reduced pressure. The residue was purified by silica gel column chromatography to give the title compound (47 mg, 58 μmol, 89%).

[Formula 36]

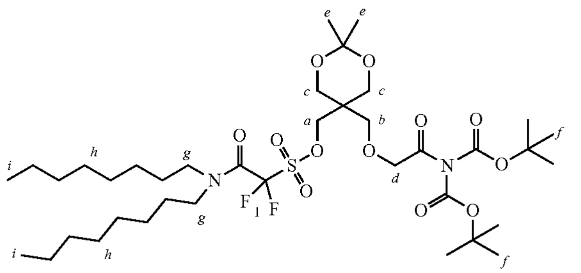

$^1$H NMR (400 MHz, $CDCl_3$) δ 4.70 (s, 2H, H-d), 4.52 (s, 2H, H-a), 3.81 (m, 4H, H-c), 3.53 (s, 2H, H-b), 3.39 (m, 4H, H-g), 1.53 (s, 18H, H-f), 1.41 (d, 6H, H-e, J=4.5 Hz), 1.27 (m, 24H, H-h), 0.881 (m, 6H, H-i);

$^{19}$F NMR (400 MHz, $CDCl_3$) δ −98.1 (s, 2F, F-1)

(5) Synthesis of (2R,3R)-5,7-dimethoxy-8-((N-methylamino)methyl)-2-(3,4,5-trimethoxyphenyl) chroman-3-ol

[Formula 37]

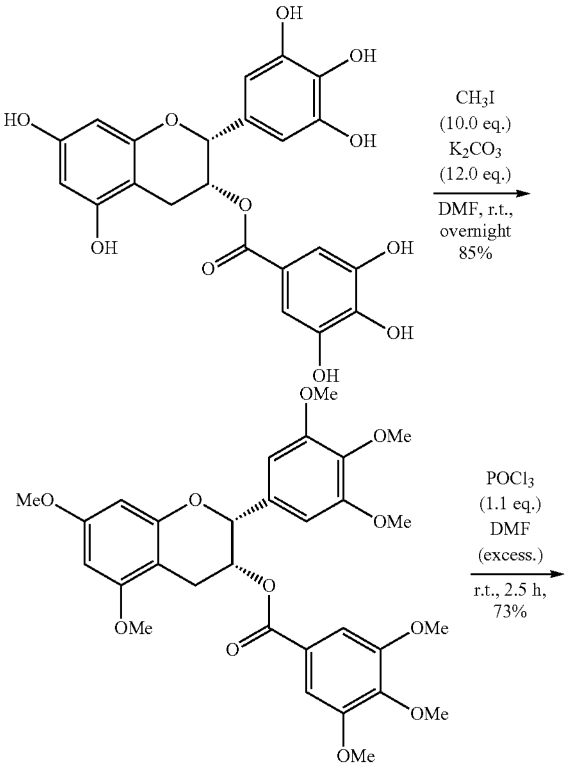

-continued

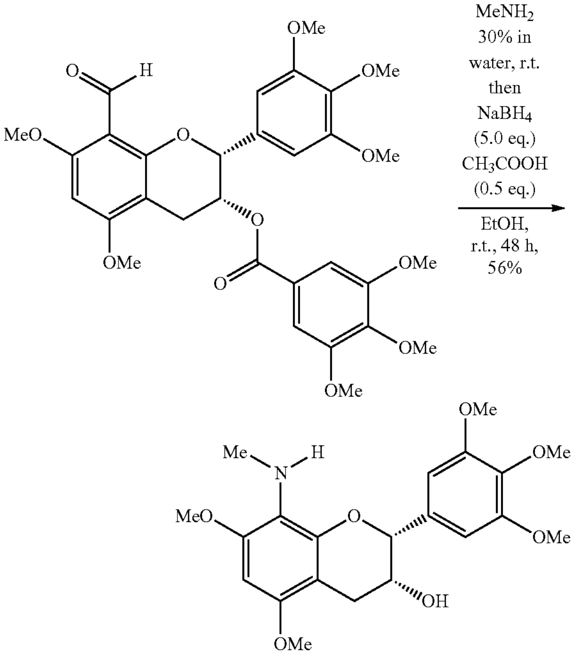

(5-1) Synthesis of (2R,3R)-5,7-dimethoxy-2-(3,4,5-triphenoxyphenyl)chroman-3-yl 3,4,5-trimethoxy-benzoate To a solution of (2R,3R)-5,7-dihydroxy-2-(3,4,5-trihydroxy)chroman-3-yl 3,4,5-trihydroxybenzoate (5.00 g, 10.9 mmol, 1.0 eq.) in dry N,N,-dimethylformamide (50 mL) were added potassium carbonate (18.1 g, 131 mmol, 12.0 eq.) and iodomethane (6.79 mL, 109 mmol, 10.0 eq.) at 0° C. After reacting at room temperature for 12 hours, the mixture was poured into a mixed solution of ethyl acetate and saturated ammonium chloride. After extracting the aqueous layer with ethyl acetate, the organic layer was washed with saturated brine. After drying the obtained organic layer over magnesium sulfate, the filtrate from which magnesium sulfate was removed by filtration was concentrated under reduced pressure. The obtained residue was purified by silica gel column chromatography to give the title compound (5.28 g, 925 mmol, 85%).

[Formula 38]

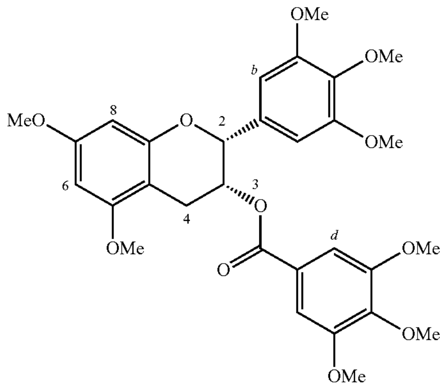

$^1H$ NMR (400 MHz, $CDCl_3$) δ 7.18 (s, 2H, H-d), 6.70 (s, 2h, H-b), 6.23 (d, 1H, H-6, J=2.4 Hz), 6.12 (d, 1H, H-8, J=2.0 Hz), 5.67 (br, 1H, H-3), 5.09 (s, 1H, H-2), 3.86-3.70 (m, 24H, H-Me), 3.05 (d, 2H, H-4, J=3.6 Hz);

(5-2) Synthesis of (2R,3R)-8-formyl-5,7-dimethoxy-2-(3,4,5-trimethoxy)chroman-3-yl 3,4,5-trimethoxybenzoate Phosphoryl chloride (180 μL, 1.93 mmol, 1.1 eq.) was added to dry N,N,-dimethylformamide (4.28 mL) at 0° C. After reacting at room temperature for 30 minutes, a solution of (2R,3R)-5,7-dimethoxy-2-(3,4,5-triphenoxyphenyl)chroman-3-yl 3,4,5-trimethoxybenzoate (1.00 g, 1.75 mmol, 1.0 eq.) in dry N,N-dimethylformamide was added at 0° C. After further stirring for 2 hours at room temperature, the reaction solution was poured into sodium bicarbonate water and ethyl acetate at 0° C. After extracting the aqueous layer with ethyl acetate, the organic layer was washed with saturated brine and then dried over magnesium sulfate. The filtrate from which magnesium sulfate was removed by filtration was concentrated under reduced pressure. The obtained residue was purified by silica gel column chromatography to give the title compound (788 mg, 1.29 mmol, 73%).

[Formula 39]

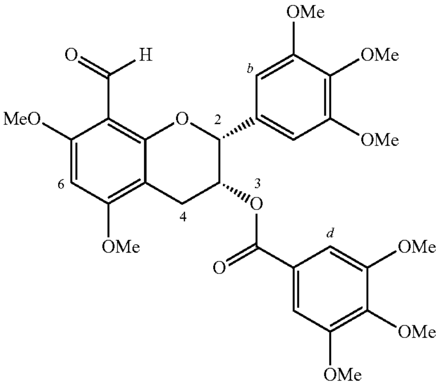

$^1H$ NMR (400 MHz, $CDCl_3$) δ 10.5 (s, 1H, H—CHO), 7.11 (s, 2H, H-d), 6.86 (s, 2H, H-b), 6.10 (s, 1H, H-6), 5.73 (br, 1H, H-3), 5.24 (s, 1H, H-2), 3.94-3.70 (m, 24H, H-Me), 3.08 (m, 2H, H-4);

(5-3) Synthesis of (2R,3R)-5,7-dimethoxy-8-((N-methylamino)methyl)-2-(3,4,5-trimethoxyphenyl) chroman-3-ol (2R,3R)-8-Formyl-5,7-dimethoxy-2-(3,4,5-trimethoxy) chroman-3-yl 3,4,5-trimethoxybenzoate (1.00 g, 1.67 mmol) was reacted in a 40% methylamine aqueous solution (20 mL, 0.24 mol) at room temperature for 24 hours. The reaction solution was poured into a mixture of methylene chloride and water, and the organic layer was washed with water. The obtained organic layer was dried using magnesium sulfate, and then concentrated under reduced pressure. The obtained residue was dissolved in ethanol (7.0 mL) and then sodium borohydride (316 mg, 8.53 mmol, 5.0 eq.) was added at 0° C. After reacting at room temperature for 24 hours, the mixture was poured into methylene chloride and water. After extracting the aqueous layer with methylene chloride, the organic layer was extracted with 1M hydrochloric acid. The aqueous layer was adjusted to pH 9 using sodium bicarbonate and potassium carbonate, and extracted using dichloromethane. The obtained organic layer was filtered with magnesium sulfate and concentrated under reduced pressure to give the title compound (390 mg, 931 μmol, 56%).

[Formula 40]

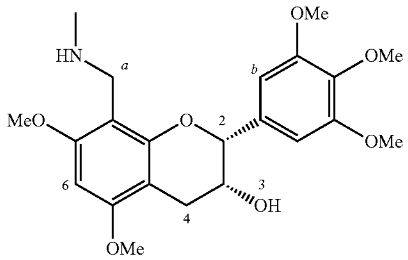

$^1H$ NMR (400 MHz, $CDCl_3$) δ 10.5 (s, 1H, H—CHO), 6.78 (s, 2h, H-b), 6.12 (s, 1H, H-6), 4.94 (s, 1H, H-2), 4.28 (br, 1H, H-3), 3.90-3.84 (m, 24H, H-Me), 3.00 (d, 2H, H-a, J=3.0 Hz), 2.89 (m, 2H, H-4), 2.39 (s, 3H, H—NHMe);

(6) Synthesis of 3,4,5-tris(methoxymethyl)benzoic acid

[Formula 41]

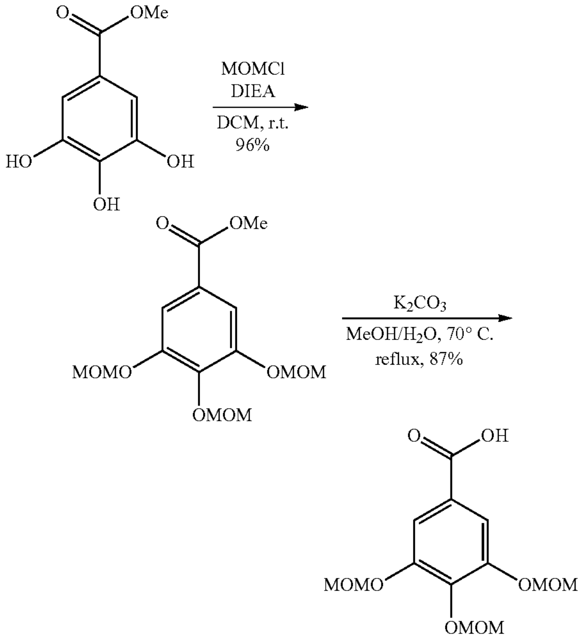

(6-1) Synthesis of methyl 3,4,5-tris(methoxymethyl)benzoate

To a solution of methyl 3,4,5-trihydroxybenzoate (1.00 g, 5.43 mmol, 1.0 eq.) in dichloromethane (54 mL) were added diisopropylethylamine (7.1 mL, 40.7 mmol, 7.5 eq.) and chloro(methoxy)methane (1.86 mL, 24.4 mmol, 4 5 eq.) at 0° C. After reacting at room temperature for 2 hours, the mixture was poured into a saturated aqueous ammonium chloride solution and ethyl acetate. The aqueous layer was extracted using ethyl acetate. The obtained organic layer was washed with saturated brine, and then dried using magnesium sulfate. The filtrate from which magnesium sulfate was removed by filtration was concentrated under reduced pressure. The obtained residue was purified by silica gel column chromatography to give the title compound (1.64 g, 5.21 mmol, 96%).

[Formula 42]

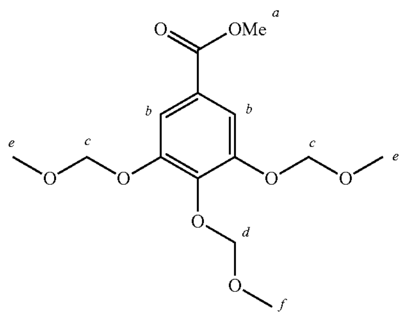

$^1$H NMR (400 MHz, $CDCl_3$) δ 7.54 (s, 2H, H-b), 5.25 (s, 4H, H-c), 5.22 (s, 2H, H-d), 3.89 (s, 3H, H-a), 3.61 (s, 3H, H-f), 3.51 (s, 6H, H-e);

(6-2) Synthesis of 3,4,5-tris(methoxymethyl)benzoic acid

To a solution of methyl 3,4,5-tris(methoxymethyl)benzoate (2-34) (623 mg, 1.97 mmol, 1.0 eq.) in methanol (3.2 mL) were added potassium carbonate (544 mg, 3.94 mmol, 2.0 eq.) and water (3.2 mL) at room temperature. After reacting at 70° C. for 2 hours, the reaction solution was poured into ammonium chloride, 1M hydrochloric acid, and ethyl acetate. The aqueous layer was extracted with ethyl acetate, then washed with saturated sodium bicarbonate aqueous solution and dried over magnesium sulfate. The obtained residue was recrystallized using chloroform and hexane to give the title compound (518 mg, 1.71 mmol, 87%).

[Formula 43]

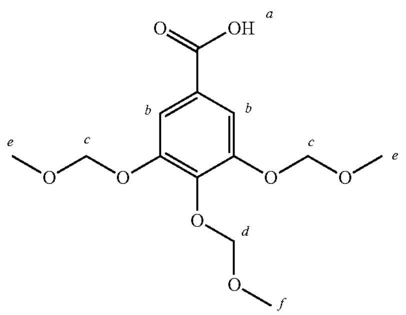

$^1$H NMR (400 MHz, $CDCl_3$) δ 7.59 (s, 2H, H-b), 5.26 (s, 4H, H-c), 5.24 (s, 2H, H-d), 3.58 (s, 3H, H-f), 3.52 (s, 6H, H-e);

(7) Synthesis of (2R,3R)-8-((2-((5-((((2-(N,N-dioctylamino)-1,1-difluoro-2-oxoethyl)sulfonyl)oxy) methyl)-2,2-dimethyl-1,3-dioxan-5-yl)methoxy)-N-methylacetamido)methyl)-5,7-dimethoxy-2-(3,4,5-trimethoxyphenyl)chroman-3-yl 3,4,5-tris (methoxymethyl)benzoate

[Formula 44]

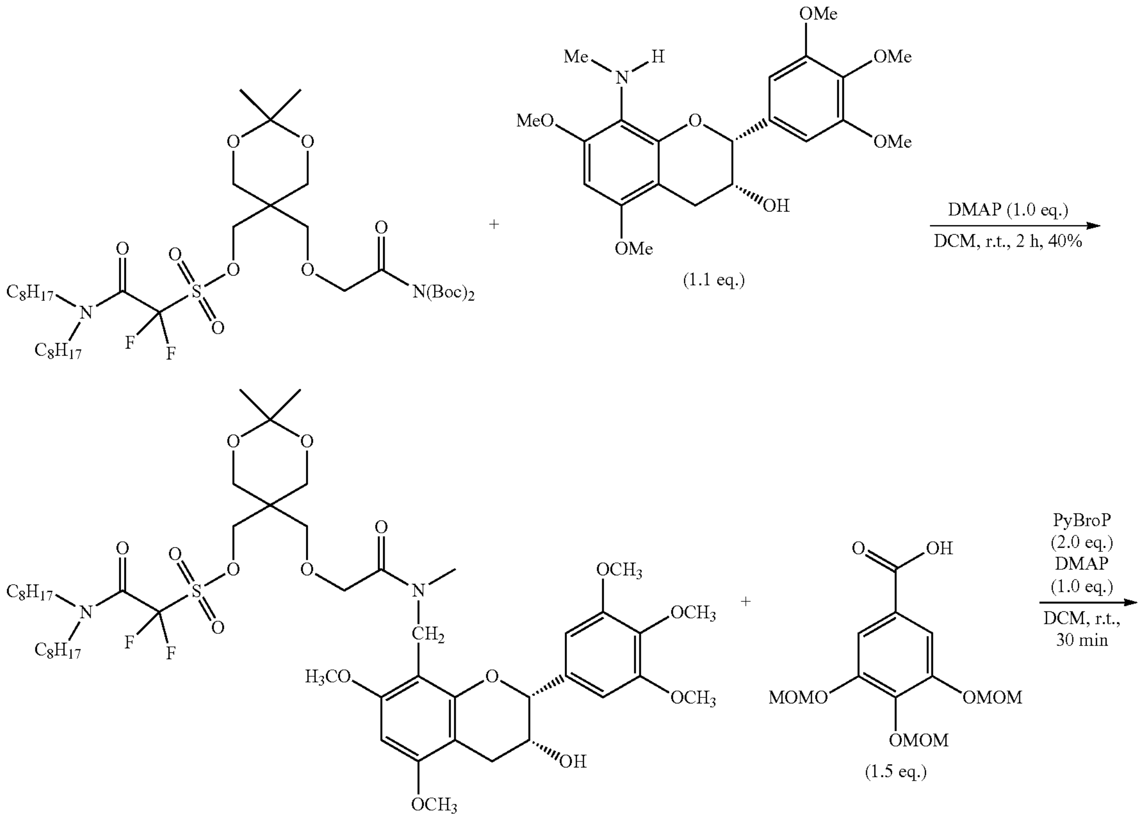

-continued

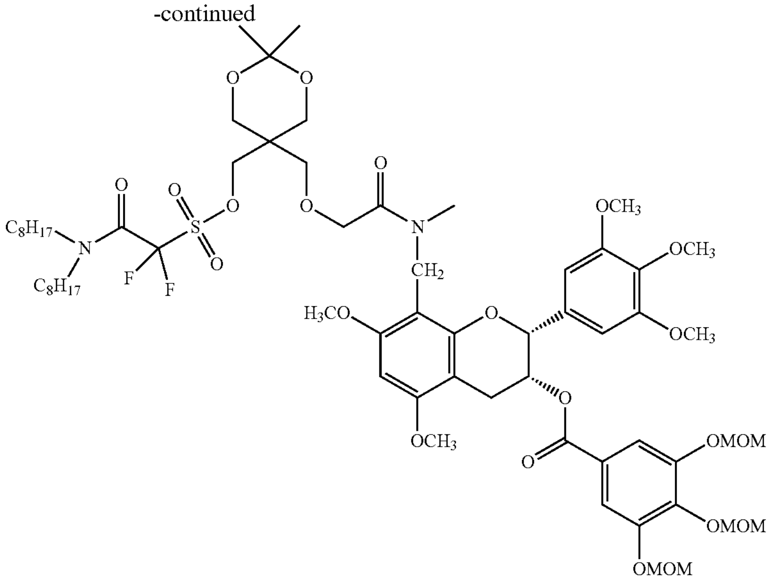

(7-1) Synthesis of (5-((2-((((2R,3R)-3-hydroxy-5,7-dimethoxy-2-(3,4,5-trimethoxyphenyl)chroman-8-yl) methyl) (N-methylamino)-2-oxoethyl)methyl)-2,2-dimethyl-1,3-dioxan-5-yl)methyl 2-(N,N-dioctylamino)-1,1-difluoro-2-oxoethane-1-sulfonate To a solution of (5-((2-(bis(tert-butoxycarbonyl)amino)-2-oxoethyl)methyl)-2,2-dimethyl-1,3-dioxan-5-yl)methyl

[Formula 45]

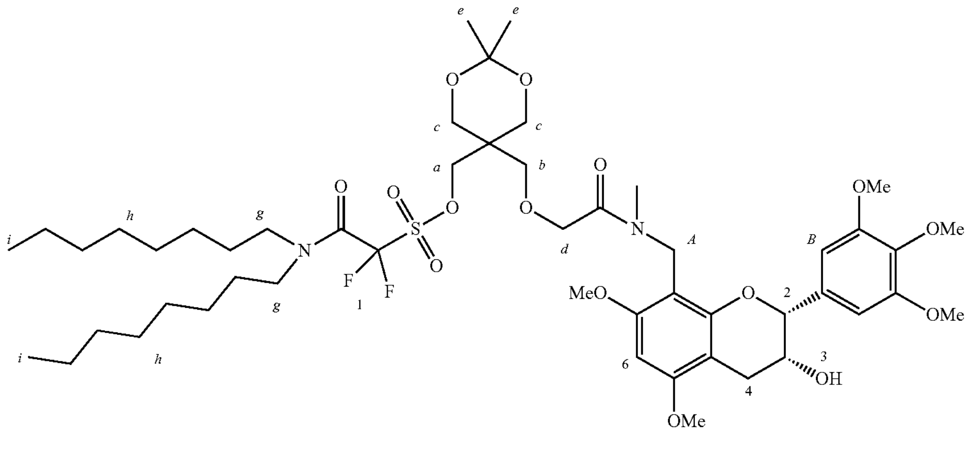

2-(N,N-dioctylamino)-1,1-fluoro-2-oxoethane-1-sulfonate (40 mg, 48 μmol, 1.0 eq.) in dry dichloromethane (1.0 mL) were added (2R,3R)-5,7-dimethoxy-8-((N-methylamino) methyl)-2-(3,4,5-trimethoxy)chroman-3-ol (24 mg, 58 μmol, 1.2 eq.) and N,N-dimethylaminopyridine (5.9 mg, 48 μmol, 1.0 eq.) at 0° C. After reacting at room temperature for 2 hours, the mixture was poured into ethyl acetate and water, and the aqueous layer was extracted using ethyl acetate. The organic layer was washed using saturated brine, and then dried using magnesium sulfate. After filtering off the magnesium sulfate, the filtrate was concentrated under reduced pressure. The concentrated residue was purified using silica gel column chromatography to give the title compound (19.3 mg, 19.0 μmol, 40%).

$^1$H NMR (400 MHz, $CDCl_3$) δ 6.75, 6.69 (s, 2H, H—B), 6.15, 6.14 (s, 1H, H-6), 4.97, 4.95 (s, 1H, H-2), 4.70, 4.68 (s, 2H, H-d), 4.34 (s, 2H, H-a), 4.24 (br, 1H, H-3), 4.12 (m, 4H, H-c), 3.92-3.82 (m, 15H, H-Me), 3.82 (m, 2H, H-A), 3.76-3.71 (m, 3H, H—NMe-), 3.41 (s, 2H, H-b), 3.41-3.34 (m, 4H, H-g), 3.02-2.87 (m, 2H, H-4), 2.79 (s, 3H, H—NHMe), 1.40 (d, 6H, H-e, J=3.5 Hz), 1.27-1.24 (m, 24H, H-h), 0.883-0.856 (m, 6H, H-i);

$^{19}$F NMR (400 MHz, $CDCl_3$) δ −98.1 (s, 2F, F-1)

(7-2) Synthesis of (2R,3R)-8-((2-((5-((((2-(N,N-dioctylamino)-1,1-difluoro-2-oxoethyl)sulfonyl)oxy)methyl)-2,2-dimethyl-1,3-dioxan-5-yl)methoxy)-N-methylacetamido)methyl)-5,7-dimethoxy-2-(3,4,5-trimethoxyphenyl)chroman-3-yl 3,4,5-tris(methoxymethyl)benzoate To a solution of (5-((2-((((2R,3R)-3-hydroxy-5,7-dimethoxy-2-(3,4,5-trimethoxyphenyl)chroman-8-yl)methyl)(N-methylamino)-2-oxoethyl)methyl)-2,2-dimethyl-1,3-dioxan-5-yl)methyl 2-(N,N-dioctylamino)-1,1-difluoro-2-oxoethane-1-sulfonate (23 mg, 23 μmol, 1.0 eq.) in dry dichloromethane (1.0 mL) were added 3,4,5-tris(methoxymethyl)benzoic acid (10 mg, 34 μmol, 1.5 eq.), bromo-tris-pyrrolidino-phosphonium hexafluorophosphate (21 mg, 45 μmol, 2.0 eq.), and N,N,-dimethylaminopyridine (2.8 mg, 23 μmol, 1.0 eq.) at 0° C. After stirring at room temperature for 15 minutes, the reaction solution was poured into a saturated aqueous ammonium chloride solution and ethyl acetate. After extracting the aqueous layer with ethyl acetate, the organic layer was washed with saturated brine and then dried using magnesium sulfate. After removing the magnesium sulfate by filtration, the filtrate was concentrated under reduced pressure. The obtained residue was purified by silica gel column chromatography to give the title compound (14.7 mg, 17 μmol, 50%).

[Formula 46]

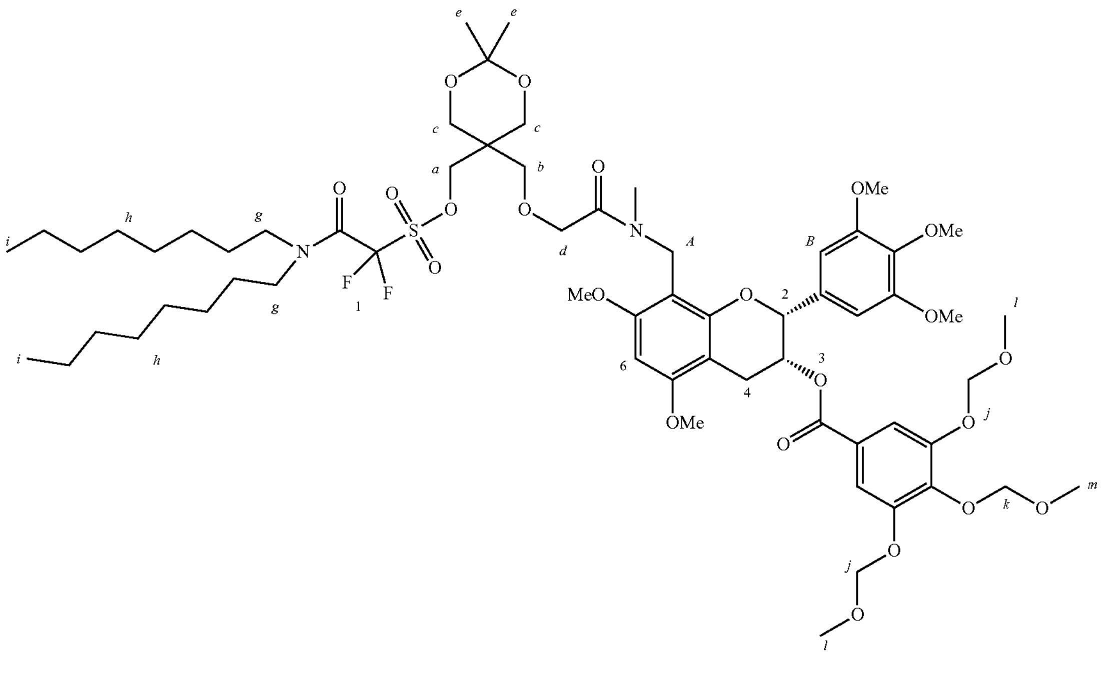

$^{1}H$ NMR (400 MHz, $CDCl_3$) δ 7.37, 7.35 (s, 2H, H-D), 6.71, 6.67 (s, 2H, H—B), 6.13 (s, 1H, H-6), 5.61, 5.64 (br, 1H, H-3), 5.20-5.11 (m, 6H, H-j, k), 5.05 (s, 1H, H-2), 4.71, 4.67 (s, 2H, H-d), 4.51-4.34 (m, 4H, H-c), 3.84-3.74 (m, 19H, H-a, A, Me), 3.56 (s, 3H, H-m), 3.44 (s, 6H, H-i), 3.42 (s, 2H, H-b), 3.40-3.34 (m, 4H, H-g), 3.06-3.00 (m, 2H, H-4), 2.86 (s, 3H, H—NHMe), 1.40 (d, 6H, H-e, J=4.0 Hz), 1.28-1.24 (m, 24H, H-h), 0.921-0.854 (m, 6H, H-i);

$^{19}F$ NMR (400 MHz, $CDCl_3$) δ −98.1 (s, 2F, F-1)

[Example 3] Reactivity and Stability of $^{211}At$ Labeling

Astatine-211 ($^{211}At$) was produced via the nuclear reaction of $^{209}Bi(\alpha,2n)^{211}At$ by irradiating a stable isotope of bismuth with an a beam by cyclotron. The isolation of $^{211}At$ from bismuth after irradiation was performed by distilling by heating in a furnace at 850° C. using a gas mixture of 20% oxygen/nitrogen as the carrier gas, and washing downstream trapping tubes with an arbitrary solvent for collecting. The $^{211}At$ solution thus obtained was concentrated by the following method and used for labeling.

(1) Concentration of $^{211}At$ Solution Using Carbonate Salt

In a previous study, it had been confirmed that the addition of 72.4 μmol of bicarbonate and carbonate salts of sodium, potassium, cesium, and the like to 100 μL of a $^{211}At$ solution collected with methanol enabled removal of the solvent with nitrogen gas while minimizing the volatilization of $^{211}At$. In the present study, potassium carbonate and cesium carbonate were dissolved in methanol and 3.6 μmol of the carbonate salt in liquid state was mixed with the $^{211}At$ solution. Then, a venting needle connected to activated carbon was attached thereto and the solvent was removed with nitrogen gas. The radioactivity of $^{211}At$ in the vials before and after solvent removal was measured to determine the residual ratio of $^{211}At$. The results are shown in Table 1.

TABLE 1

Residual ratio of $^{211}At$ in vials after solvent removal

| Type of base | Residual ratio of $^{211}At$ | Number of trials |
|---|---|---|
| No base | 37% ± 26% | 2 |
| $K_2CO_3$ (solid, 72.4 μmol) | 98% ± 2% | 29 |
| $Cs_2CO_3$ (solid, 72.4 μmol) | 99% ± 1% | 2 |

TABLE 1-continued

| Residual ratio of $^{211}At$ in vials after solvent removal | | |
|---|---|---|
| Type of base | Residual ratio of $^{211}At$ | Number of trials |
| $K_2CO_3$ (liquid, 3.6 μmol) | 96% ± 3% | 3 |
| $Cs_2CO_3$ (liquid, 3.6 μmol) | 96% ± 3% | 3 |

(2) $^{211}At$ Labeling of Labeling Precursor Having Novel Leaving Group

After the solvent removal under each of the two conditions of 3.6 μmol of a liquid carbonate salt in the bottom of Table 1, labeling precursors A and B (2.2 μmol/100 μL) dissolved in anhydrous acetonitrile were added to the concentrated $^{211}At$ and mixed therewith well by a vortex mixer. The labeling precursors were allowed to act at room temperature and 60° C., and the rate of formation of the $^{211}At$-labeled compound (C) was determined by TLC. 1 μL of the reaction solution was spotted on TLC over time, and then developed with hexane:ethyl acetate=4:1 after 2 minutes, and the rate of formation of C was measured by autoradiography. The results are shown in Table 2. To confirm that the precursor was less damaged when B was used than when A was used, the changes in the TLC spots when exposed to 254 nm UV light were checked (FIG. 1).

[Formula 47]

A

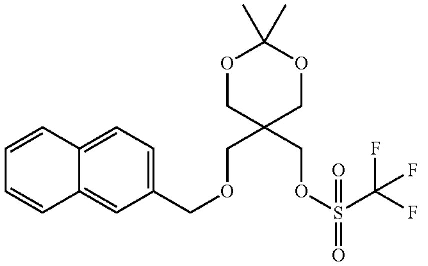

B

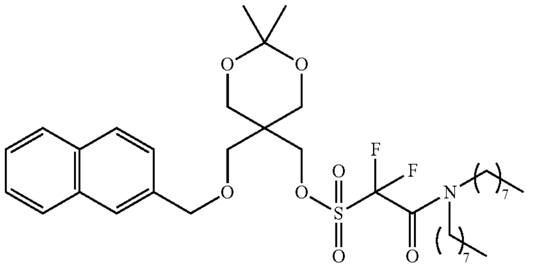

C

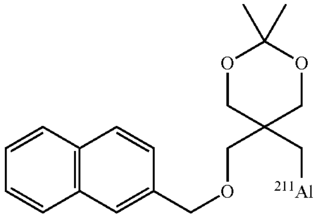

TABLE 2

| Rate of formation of $^{211}At$-labeled compound of labeling precursors A and B | | | | |
|---|---|---|---|---|
| Carbonate salt | Temperature | Reaction time (min) | Rate of formation (%) A | B |
| $K_2CO_3$ | Room temperature | 1 | 30 | 11 |
| | | 5 | 49 | 19 |
| | | 15 | 57 | 30 |
| | | 30 | 52 | 43 |
| | | 60 | 57 | 56 |
| | 60° C. | 10 | 70 | 80 |
| | | 30 | 69 | 83 |
| $Cs_2CO_3$ | Room temperature | 1 | 30 | 10 |
| | | 5 | 48 | 14 |
| | | 15 | 52 | 24 |
| | | 30 | 50 | 35 |
| | | 60 | 56 | 51 |
| | 60° C. | 10 | 64 | 81 |
| | | 30 | 72 | 81 |

The leaving group (CDf8) of the labeling precursor B, which was developed in the present study, was designed taking into account the expectation that it had a lower acidity than triflate, the leaving group of A, and a higher acidity than tosyl (acidity pKa: triflate=−14, tosyl=0.7). Therefore, the labeling precursor B is expected to be a precursor that is more reactive than a precursor having a tosyl group and appropriately more stable than a precursor having a triflate group. In the present study, TLC analysis confirmed that At labeling of the labeling precursor B proceeded sufficiently. In addition, a large number of spots on the TLC were confirmed over time for A, which had a triflate group, and it indicates degradation (FIG. 1, top); in contrast, it was found that there was less damage of the precursor B (FIG. 1, Bottom).

All publications, patents and patent applications cited herein are incorporated by reference in their entirety.

INDUSTRIAL APPLICABILITY

Since radioactive halogen-labeled compounds can be used in medicaments, the present invention can be used in industries related to medicaments.

The invention claimed is:

1. A compound represented by the following general formula (I):

[Formula 1]

(I)

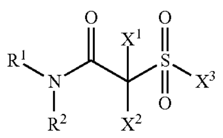

wherein $R^1$ and $R^2$ each independently represent an alkyl group having 5 to 20 carbon atoms, $X^1$ and $X^2$ each independently represent a halogen atom, and $X^3$ represents a halogen atom.

2. The compound according to claim 1, wherein $R^1$ and $R^2$ in the general formula (I) are each an alkyl group having 7 to 11 carbon atoms.

3. The compound according to claim 1, wherein $X^1$ and $X^2$ in the general formula (I) are each a fluorine atom or a chlorine atom.

4. A compound represented by the following general formula (II):

[Formula 2]

(II)

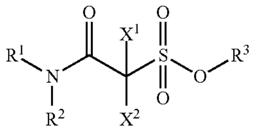

wherein $R^1$ and $R^2$ each independently represent an alkyl group having 5 to 20 carbon atoms, $X^1$ and $X^2$ each independently represent a halogen atom, and $R^3$ represents (i) a monovalent group derived from a sugar, which is a monovalent group obtained by removing one hydrogen atom in the sugar; (ii) a monovalent group derived from a peptide, which is a monovalent group obtained by removing one hydrogen atom in the peptide; or (iii) a group represented by the following general formula (A) or (B):

[Formula 3]

(A)

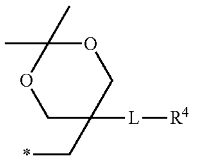

-continued

[Formula 4]

(B)

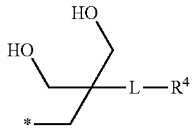

wherein L represents a divalent group that functions as a spacer, $R^4$ represents an aryl group optionally substituted with a substituent, a heteroaryl group optionally substituted with a substituent, or an aminocarbonyl group optionally protected by a protective group, and * represents a bonding site.

5. The compound according to claim 4, wherein $R^1$ and $R^2$ in the general formula (II) are each an alkyl group having 7 to 11 carbon atoms.

6. The compound according to claim 4, wherein $X^1$ and $X^2$ in the general formula (II) are each a fluorine atom or a chlorine atom.

7. The compound according to claim 4, wherein L in the general formula (A) or (B) is an alkylene group, and one or more $-CH_2-$ of the alkylene group are optionally replaced with —O— or a phenylene group.

8. The compound according to claim 4, wherein $R^4$ in the general formula (A) or (B) is a 4-[2,3-bis(tert-butoxycarbonyl)guanidinomethyl]phenyl group, a naphthalen-2-yl group, a 2-nitro-1H-imidazol-1-yl group, or an aminocarbonyl group protected by a tert-butoxycarbonyl group.

9. A reagent for producing a labeling precursor compound, comprising the compound according to claim 1.

10. A labeling precursor reagent for a radioactive halogen-labeled compound, comprising the compound according to claim 4.

* * * * *